(12) United States Patent
Hanna et al.

(10) Patent No.: US 12,329,868 B2
(45) Date of Patent: Jun. 17, 2025

(54) SYSTEM FOR VEHICLE STERILIZATION

(71) Applicant: Our Shields LLC, Government Camp, OR (US)

(72) Inventors: Kirk D. Hanna, Portland, OR (US); Derek J. Hanna, Milwaukie, OR (US)

(73) Assignee: Our Shields LLC, Government Camp, OR (US)

( * ) Notice: Subject to any disclaimer, the term of this patent is extended or adjusted under 35 U.S.C. 154(b) by 106 days.

(21) Appl. No.: 17/389,168

(22) Filed: Jul. 29, 2021

(65) Prior Publication Data

US 2022/0031889 A1 Feb. 3, 2022

Related U.S. Application Data

(60) Provisional application No. 63/187,005, filed on May 11, 2021, provisional application No. 63/161,839, (Continued)

(51) Int. Cl.
*A61L 2/20* (2006.01)

(52) U.S. Cl.
CPC .......... *A61L 2/202* (2013.01); *A61L 2202/11* (2013.01); *A61L 2202/14* (2013.01); *A61L 2202/25* (2013.01)

(58) Field of Classification Search
CPC .. A61L 2209/12; A61L 2209/16; A61L 9/122; A61L 9/20; A61L 9/04; A61L 9/18; A61L 2/202; A61L 2/10; A61L 2/0047; A61L 2202/11; A61L 2202/14; A61L 2202/25; A61L 2209/111; A61L 2209/14; A61L 2209/212; A61L 9/015; A61L 2/24; A61L 2202/16; A61L 2209/11; A61L 9/22; A61L 2202/13; B60H 2003/0675; B60H 3/0616; B60H 3/0625; B60H 3/0633; B60H 3/0641; B60H 1/12; B60H 2003/0666; B60H 2003/0691; B60H 3/0035; B60H 1/00378; B60H 2003/057; B60H 3/007; B60H 3/0071; B60H 3/0078; B60H 3/014; B01D 53/76; B01D 53/72; B01D 53/66; B01D 53/0454; B01D 2251/104; B01D 2257/91; B01D 2253/102; B01D 2257/90; B01D 2259/4566; B01D 53/86;
(Continued)

(56) References Cited

U.S. PATENT DOCUMENTS 7,658,891 B1 * 2/2010 Barnes ................... C01B 13/11
128/205.28
2003/0039577 A1 * 2/2003 Nelson ...................... A61L 9/20
422/4
(Continued)

FOREIGN PATENT DOCUMENTS

CN 2191666 Y * 3/1995
EP 2488223 B1 * 1/2019 ............. A61L 2/202

OTHER PUBLICATIONS

Feng et al. (CN 2191666 Y, machine translation) (Year: 1995).*

*Primary Examiner* — Xiuyu Tai
(74) *Attorney, Agent, or Firm* — Chernoff, Vilhauer, McClung & Stenzel LLP

(57) ABSTRACT

A system for sanitizing the interior of vehicles that provides an integrated computer system, a body that contains the components of the system, devices for transferring ozone to a vehicle, and a sterilizer for removing ozone from the vehicle.

8 Claims, 43 Drawing Sheets

Related U.S. Application Data filed on Mar. 16, 2021, provisional application No. 63/148,014, filed on Feb. 10, 2021, provisional application No. 63/105,048, filed on Oct. 23, 2020, provisional application No. 63/059,681, filed on Jul. 31, 2020.

(58) Field of Classification Search
CPC ........ B01D 2259/4583; C01B 2201/82; C01B 13/10; C01B 13/11; Y02P 20/151; A62B 17/006; F24F 8/26; F24F 6/00; F24F 8/40; F24F 8/20
See application file for complete search history.

(56) References Cited

U.S. PATENT DOCUMENTS

| | | | | |
|---|---|---|---|---|
| 2011/0064607 | A1* | 3/2011 | Hedman | A61L 2/06 422/1 |
| 2012/0063949 | A1* | 3/2012 | Jennings | F24F 8/26 422/295 |
| 2017/0072082 | A1* | 3/2017 | Jurak | A61L 2/10 |
| 2018/0214823 | A1* | 8/2018 | Faudry | B01D 53/72 |
| 2022/0008597 | A1* | 1/2022 | Bergman | A61L 2/24 |

* cited by examiner

☐ This Vehicle is sterilized after every rider with handheld UV-C Sterilizer by the driver, the passenger can also use UV-C sterilizer
☐ This Vehicle is shocked weekly with the "Smart Ozone Sterilizer Tower"
☐ You can check the last time this vehicle was shocked with Ozone Sterilizer by entering SXY324 License plate number

UV-C Handheld Sterilizer

GermSterilizer.com Handheld UV-C Sterilizer utilizes UV light to eliminate pathogens on any surface in seconds. The Germicidal UV-C kills microorganisms by destroying their nucleic acids and disrupting their DNA, leaving them unable to perform vital cellular functions.

For rapid spot cleaning on all kinds of surfaces. Simply Shine the UV-C light on the desired area. Just takes a few seconds to sterilize any area that has been exposed to pathogens. Quick spot sterilization for areas that have been exposed to potential pathogens

CAUTION – YOU MUST WEAR UV EYE PROTECTION GLASSES

Smart Ozone Sterilizer Tower

GermSterilizer.com Smart Ozone Tower Ozone Triatomic Oxygen Generator -produces high levels of ozone gas ions that destroys 99.9% potentially harmful pathogens for EMS, Police, ride share and the public. After the ozone ion fumigation cycle finishes, the Scrubber Technology removes all remaining ozone within minutes by converting it to oxygen, allowing fast and safer access to the sterilized vehicles.

CAUTION – No Humans, pets or food can be in vehicle

GERMSTERILIZER.COM KILLS GERMS & VIRUSES

Virus Free Zone
99.%
Check Sterilized Date
Plate #: SXY324

ALL-IN-ONE STERILIZER

UV-C Handheld Sterilizer is pulled out of cylinder and used by driver & Rider to sterilize vehicle interior after each customer.

UV-C Handheld Sterilizer is inserted in cylinder to kill 99.9% airborne germs and viruses while removing odors in the vehicle 250 CFM Blower
Carbon Filter Sterilized Air
You can move & adjust vent

FIG. 8

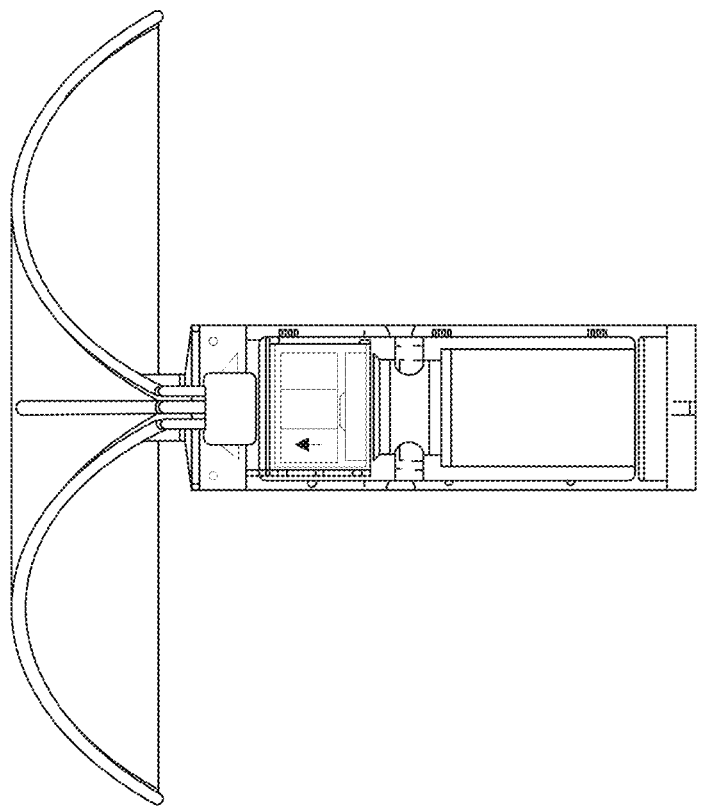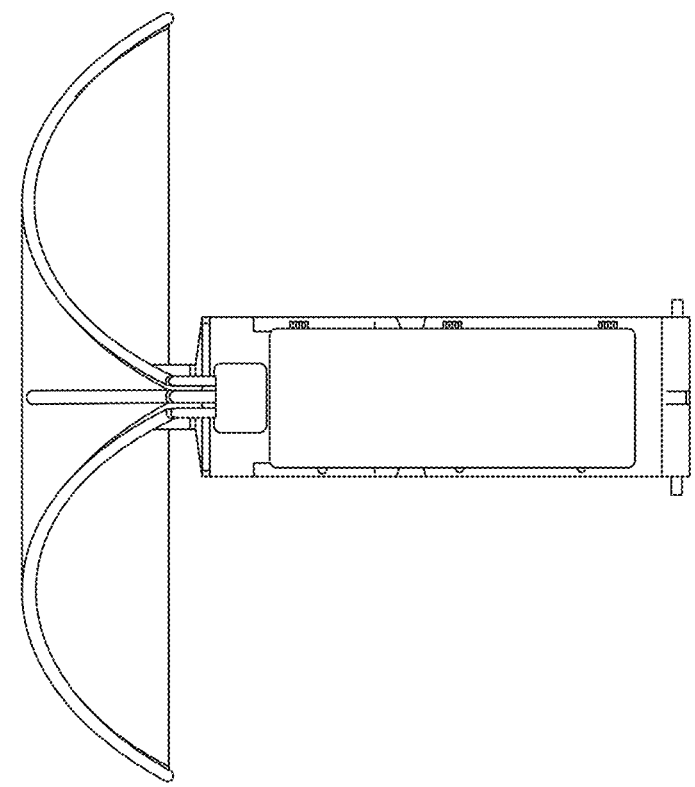
FIG. 9A

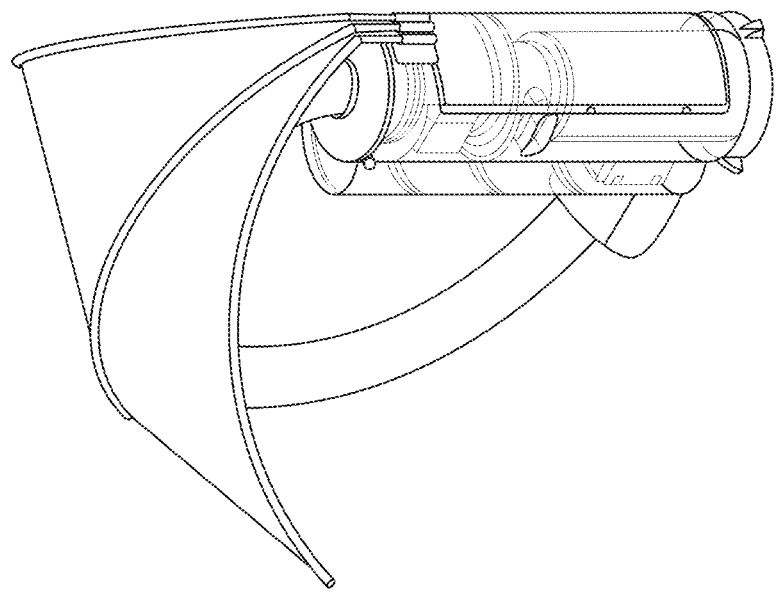
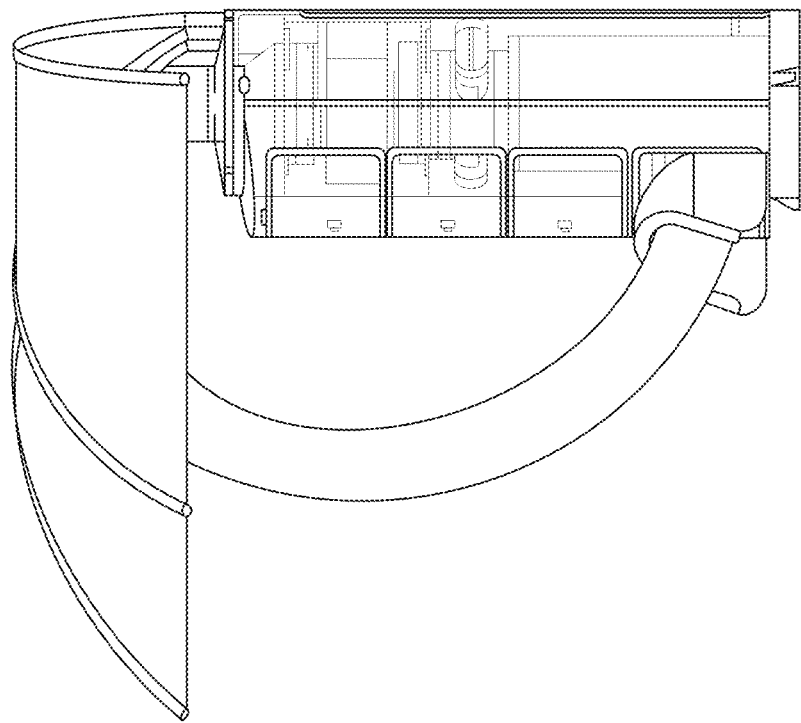
FIG. 9B

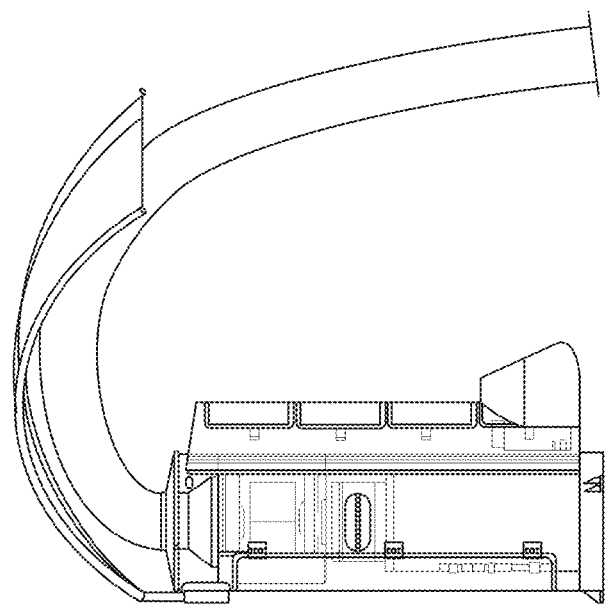
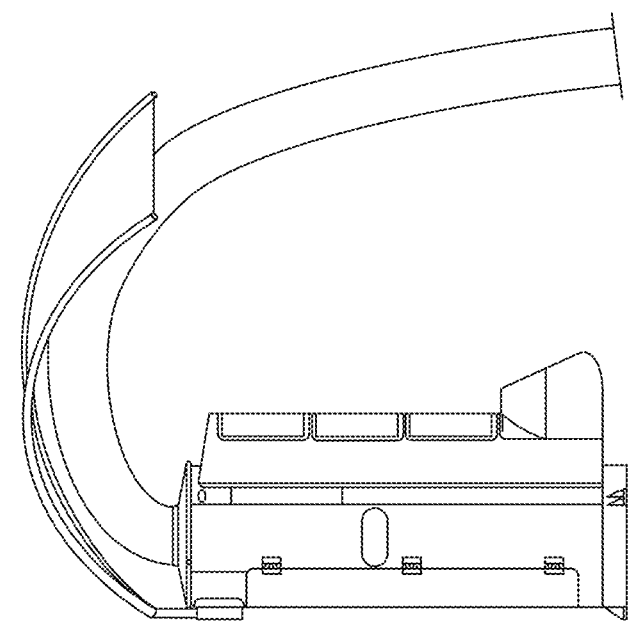
FIG. 9C

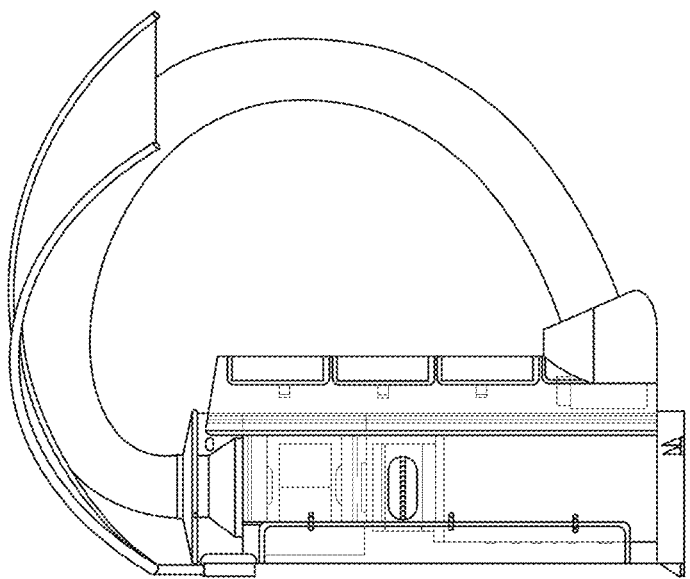
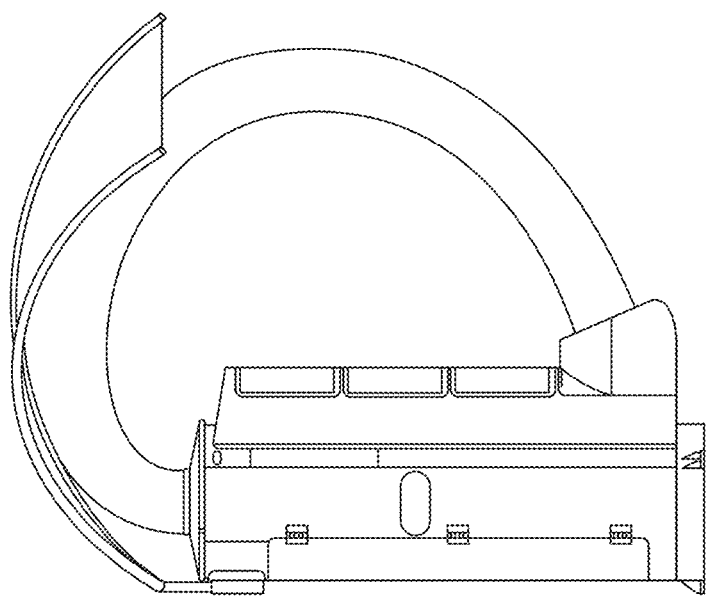
FIG. 9D

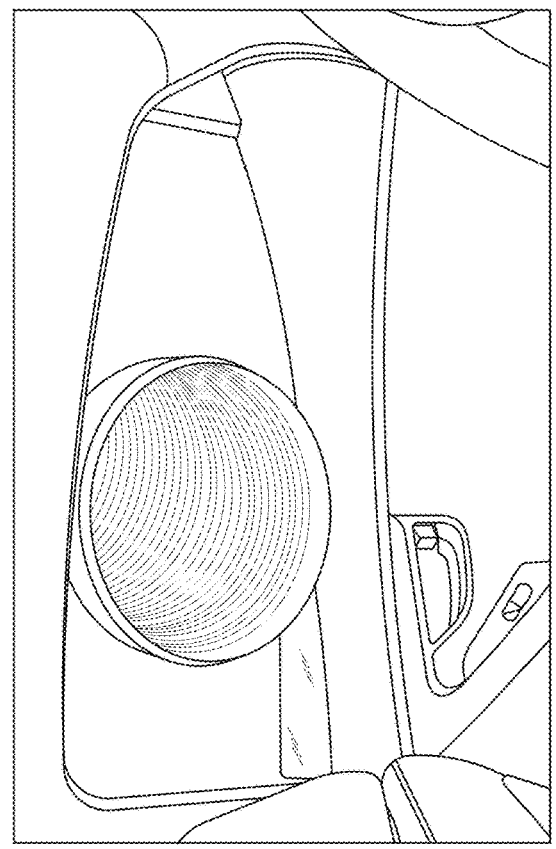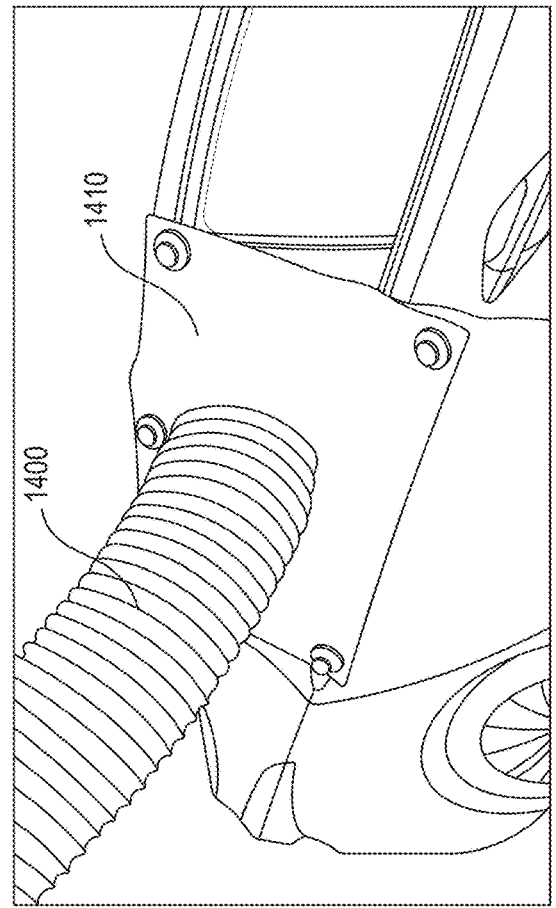
FIG. 14

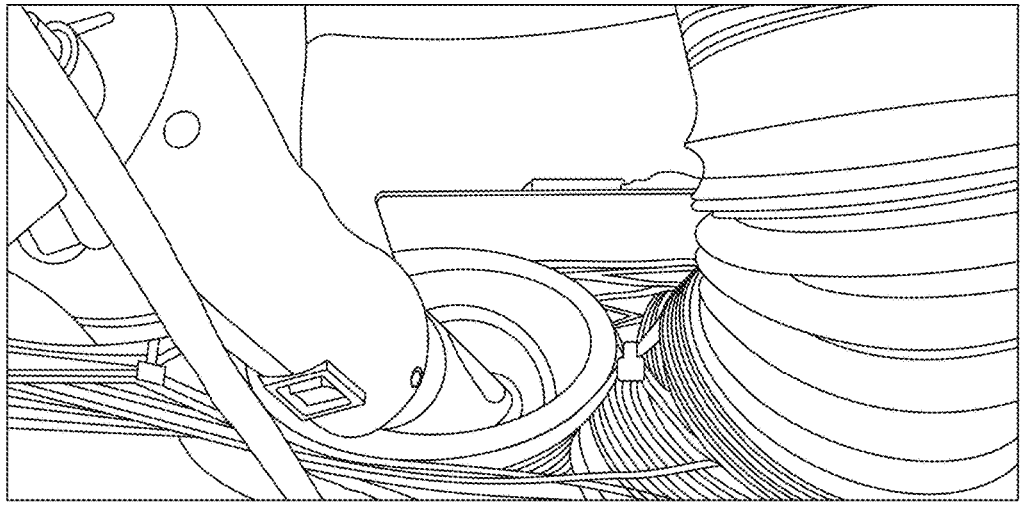
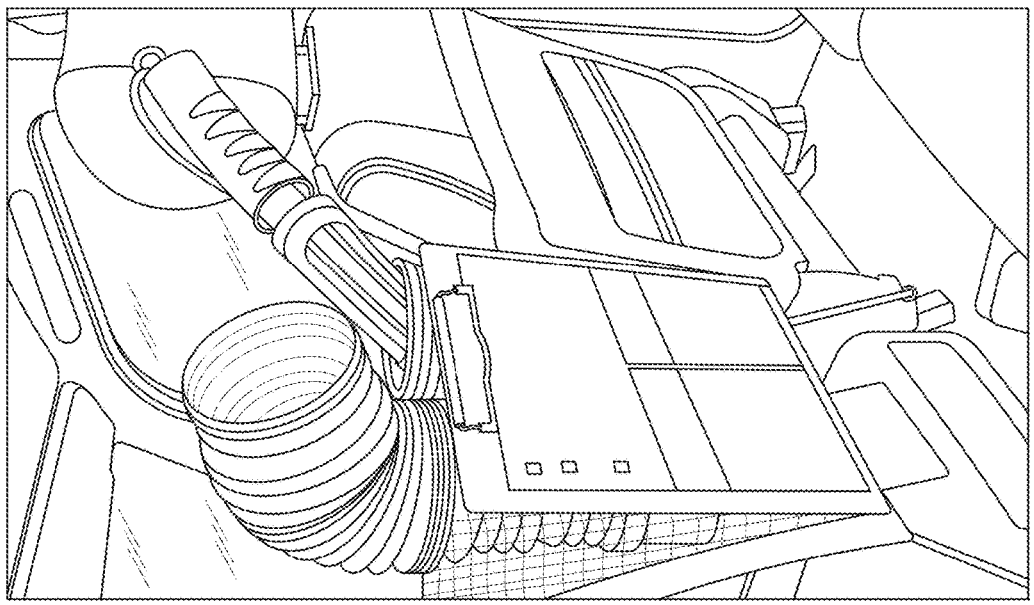
FIG. 16

SYSTEM FOR VEHICLE STERILIZATION

CROSS REFERENCE TO RELATED APPLICATIONS

This application claims the benefit of U.S. Provisional Patent Application No. 63/187,005 filed May 11, 2021; claims the benefit of U.S. Provisional Patent Application No. 63/161,839 filed Mar. 16, 2021; claims the benefit of U.S. Provisional Patent Application No. 63/148,014 filed Feb. 10, 2021; claims the benefit of U.S. Provisional Patent Application No. 63/105,048 filed Oct. 23, 2020; and claims the benefit of U.S. Provisional Patent Application No. 63/059,681 filed Jul. 31, 2020.

BACKGROUND OF THE INVENTION

The present invention relates to a sterilization and disinfection system, and more particularly, to a sterilization and disinfection system which sterilizes and/or disinfects the interior of a space, especially passenger cars, busses, boats, trains, stadiums, ski lifts, classrooms, offices, etc., by using an ozone sterilization process and/or a UV sterilization process.

Sterilization is the killing of viruses, bacteria, fungi, or other microorganisms, either in the growing or dormant spore state. Conventional sterilization processes include the use of high temperature (such as steam and dry heat) or the use of toxic chemicals. Steam pressure sterilization is a time-honored sterilization method that is fast and cost effective. However, steam pressure sterilization can damage electronic equipment, upholstery, and other materials or devices found within most vehicles. Thus, to properly sanitize cars, buses, trucks, or other types of vehicles different sterilization techniques are desirable.

An efficient, safe, and inexpensive sterilization agent is ozone ($O_3$). Ozone, especially humidified ozone, is a sterilizing gas. Ozone can be generated from oxygen, especially hospital grade oxygen. Additionally, oxygen is readily available in most environments as it is a primary in the earth's atmosphere.

Ozone is widely used in industry as an oxidizing agent to bleach paper pulp, treat drinking water, and sterilize sewage water and food products. However, high concentrations are required to make ozone an effective sterilant of micro-organisms. Those high concentrations of ozone gas are necessary to allow the ozone to sufficiently penetrate the protective shells of micro-organisms.

Sterilization with ozone is more efficient and quicker than many other sterilization processes and requires few changes in user habits. Moreover, ozone-based processes are compatible for use with current vehicular materials, such as upholstery, and the electrical devices found within vehicles.

Ozone sterilization requires substantially no cooling down of sterilized surfaces, which can be used immediately following ozone sterilization. Ozone sterilization offers several other advantages. It produces no toxic waste, does not require the handling of dangerous gas cylinders, and poses no threat to the environment or the user's health at acceptable levels. Natural and synthetic materials as well as electronic components can be treated simultaneously, which for vehicle owners will obviate the need for separate sterilizers or sterilization procedures.

In general, since vehicles, particularly ride-share cars, buses, or other forms of transportation that cater to the public, are frequently used by many people, it is desirable to disinfect the interior of the vehicle regularly for public hygiene. In recent years, disinfecting the interior of vehicles is also important to prevent the spread of respiratory diseases such as SARS, swine flu, and COVID-19. There is a great need for regular effective sterilization or disinfection. In addition, even in the case of personal passenger cars, it is desirable to sterilize molds and bacteria in the air conditioners and air inlets, and to remove odors and keep the interior clean. Since there is a desire to keep interiors clean, a simple and efficient sterilization techniques for the interior of the vehicle is desired to maintain the interior cleanliness.

Currently, automated cleaning systems for cleaning the exterior of vehicles, such as car washes, are widely used for maintaining the cleanliness of vehicles. However, only the exterior of the vehicle is cleaned as the application of water is used as the primary cleaning liquid. Water is harmful to a vehicle's interior components resulting in concerns if trying to use it for cleaning the inside of a vehicle. Presently there are no devices that can be used in commercial settings to disinfect high numbers of vehicles, particularly multiple vehicles at once.

What is desired is an easy-to-use, effective, sterilization system that can be used to sterilize the interior of vehicles and environments that does not damage the vehicle's or environment's interior or cause harm to the drivers or passengers or occupants of the vehicle or environment.

BRIEF DESCRIPTION OF THE DRAWINGS

FIG. 8 illustrates a virus free sticker.

FIG. 9, FIGS. 9A-9D, illustrate a more detailed view of the sterilization tower of FIG. 7.

FIG. 14 illustrates a hose with a window adapter.

FIG. 16 illustrates the sterilization device of FIG. 15 with the ultraviolet light sterilizing the air.

DETAILED DESCRIPTION OF PREFERRED EMBODIMENTS

Over time, especially for ride sharing services, the number of different people getting into and getting out of vehicles is substantial. The duration that each person is within the vehicle varies depending on the distance to be traveled, together with traffic conditions, using the ride sharing service. Each person getting into a vehicle has a tendency to bring viruses, bacteria, fungi or other microorganisms with them, either exhaled from within their body such as in the case of CV19 or otherwise on their clothing, skin, or baggage, and leave them deposited within the interior of the vehicle. Over time, with a substantial number of people entering and exiting the vehicle, the accumulation of such viruses, bacteria, fungi, or other microorganisms increases until such a point that the additional passengers of the ride sharing service may tend to get sick from exposure to the accumulation. Also, the driver of the vehicle likewise has a tendency to become sick with a substantial number of passengers entering and exiting the vehicle by exposure to such accumulation of viruses, bacteria, fungi or other microorganisms.

A system by which the driver may track the sterilization of their vehicle is desirable so they can reduce their likelihood of becoming sick. Moreover, a system by which the passenger may be aware of the sterilization of a particular vehicle at a particular time is desirable so they can likewise reduce their likelihood of becoming sick. Further, based upon the sterilization of a particular vehicle, the passenger may select an alternative vehicle that has more recent sterilization or otherwise a more frequent sterilization, than a vehicle lacking in such respects.

Figure 1:
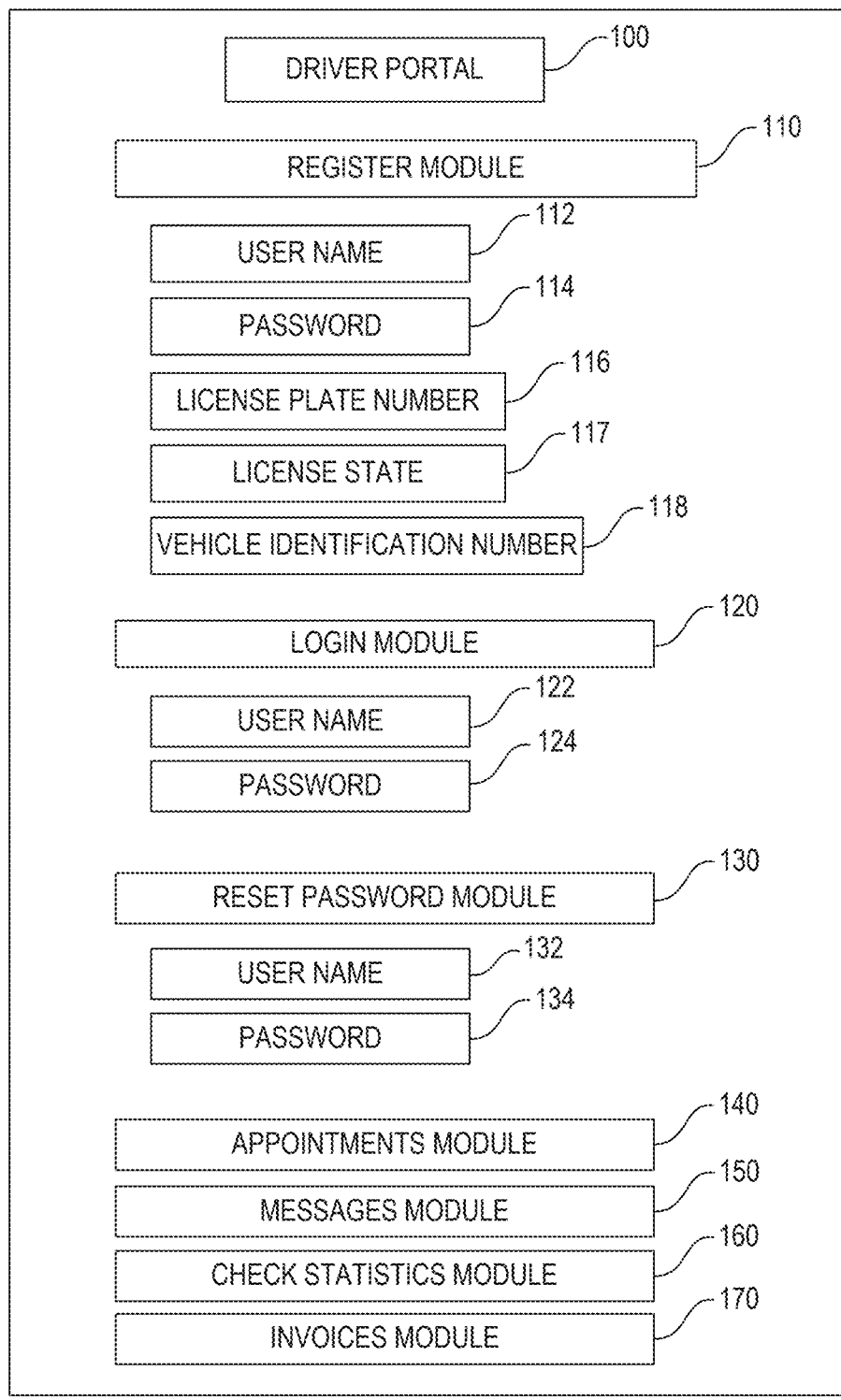
FIG. 1 illustrates a driver portal.

Referring to FIG. 1, one technique for providing tracking of the sterilization of a vehicle is for the driver to sign up with an Internet (e.g., network) based driver portal 100 together with providing a profile of their vehicle. The Internet-based driver portal 100 may be accessed by any network enabled device, such as a mobile phone, computer tablet, laptop computer, and/or desktop computer. The Internet-based portal may be in the form of a webpage, a progressive web application, a desktop/laptop/tablet-based application, a mobile device-based application, or otherwise. Data related to the sterilization of the vehicle may be uploaded in any suitable manner to the Internet-based driver portal 100. The data may relate to the service that is performed, including for example, duration of the service, the time of the service, the date of the service, an ozone service, an UV service (including UV-C), or otherwise. Data from the Internet-based driver portal 100 may be downloaded, processed, or otherwise viewed in any suitable manner to potential passengers and otherwise, such as fleet management system (e.g., Uber, Lyft, Grab, and Taxi Fleets). Data related to the sterilization of the vehicle may be provided in any suitable manner to potential passengers.

The driver portal 100 may include a register module 110. The register module 110 permits the driver to register with the system, preferably with a combination of a user name 112 and a password 114. Preferably, the user name 112 was set up by an administrator prior to the user registering through the driver portal 100. The registration also preferably includes the license plate number 116 for the vehicle, including the state 117 for the license plate number 116. The registration also preferably includes a vehicle identification number 118 of the vehicle. The system may verify that the license plate number 116 corresponds to the vehicle identification number 118 for verification purposes.

The driver portal 100 may include a login module 120. The login module 120 permits the driver to log into the system, preferably using the combination of a user name 122 and a password 124 that the driver selected as a result of their use of the register module 110. The user, based upon their status as a driver, is permitted to access portions of the system and not permitted to access other portions of the system.

The driver portal 100 may include a reset password module 130. The reset password module 130 permits the driver to reset their password to use the system. Preferably, the system requires the driver to enter their user name 132, in which a two-factor authentication is used to then reset the password 134, such as a text message, phone call, or e-mail message.

The driver portal 100 may include an appointments module 140. The appointments module 140 may include a calendar or a list of related appointments when the vehicle was sterilized, preferably including date and time, in the past and includes future scheduled sterilization appointments for the vehicle. The appointments may include a date, a time, and a location for which the driver has appointments for the sterilization in the future and completed sterilizations in the past. These calendar appointments may be set up by a fleet management and/or the driver system to ensure that proper sterilization of the vehicle is performed.

The driver portal 100 may include a messages module 150. The messages module 150 may be used by the driver to send messages and receive messages, preferably in a secure and private manner, with others. The messages module 150 may include an interface that permits sending and receiving messages from a fleet manager and/or a potential passenger. The messages module 150 may include an interface that permits sending and receiving messages with other drivers. The messages module 150 may include an interface that permits sending and receiving messages with those providing sterilization services. In addition, the messages may be synchronized with a messaging application (e.g., iMessages or text messages) of a mobile device, such as a mobile phone.

The driver portal 100 may include a check statistics module 160. The check statistics module 160 may be used to view a variety of different statistics of interest to the driver, the fleet manager, and/or the potential passenger. For example, the check statistics module may indicate the number of days until the next sterilization service. For example, the check statistics module may indicate the number of days since the previous sterilization service. For example, the check statistics module may indicate the duration of the previous sterilization service. For example, the sterilization service may include the number of passengers that have been serviced since the last sterilization.

The driver portal 100 may include an invoices module 170. The invoices module 170 may include a copy of each invoice that has been paid and those invoices yet to be paid by the driver. The driver typically pays for activities, such as sterilizations. The system may provide the driver reminders that outstanding invoices need to be paid.

The driver portal may include any other modules and/or expanded functionality, as desired, to facilitate interaction with the driver and other aspects of the system.

Figure 2A:
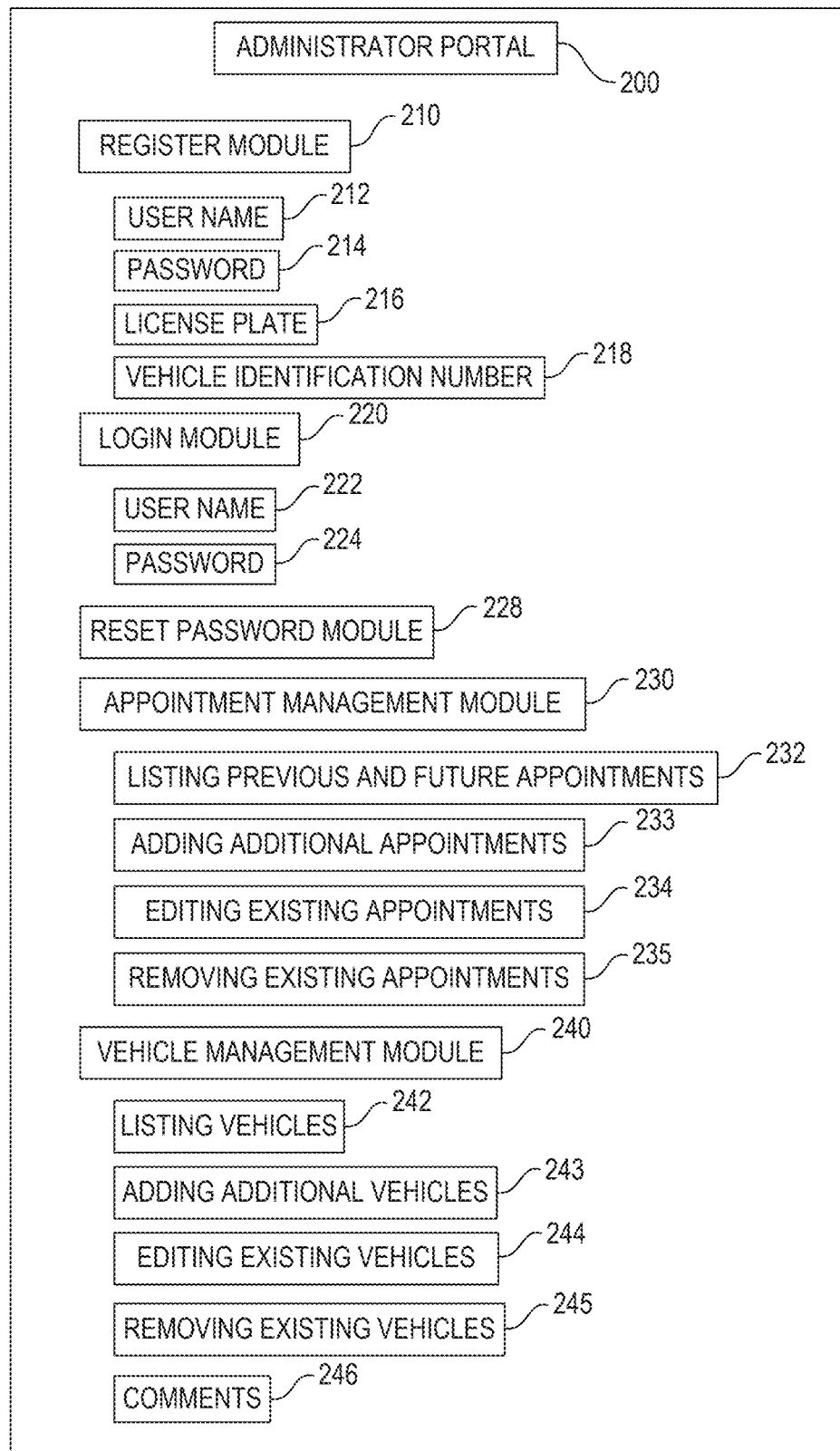
FIG. 2A and FIG. 2B illustrate an administrator portal 200.
Figure 2B:
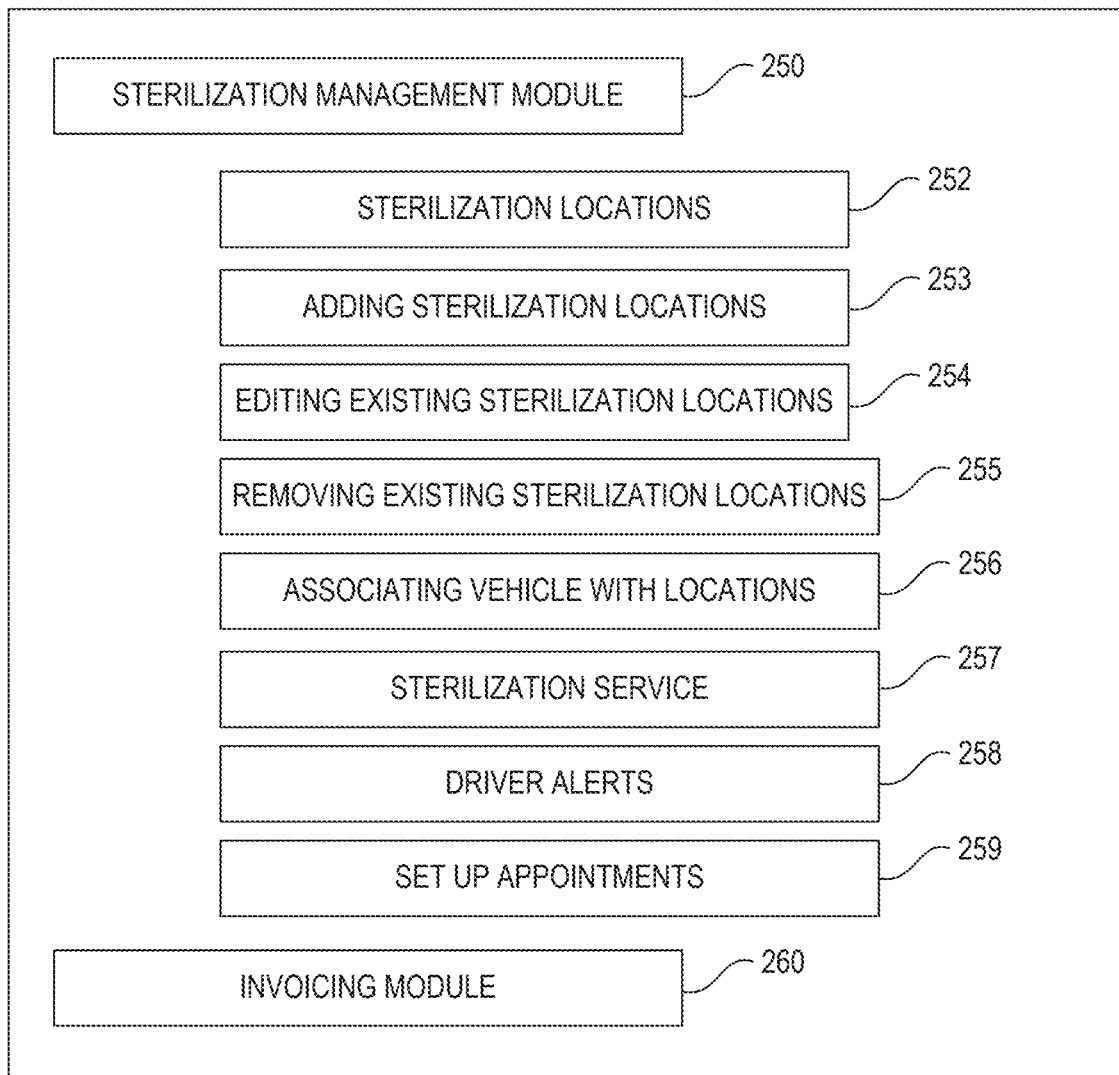

Referring to FIG. 2A and FIG. 2B, it is desirable for fleet managers, inclusive of Uber fleet managers, Lyft fleet managers, Taxi Fleet managers, system public riders, administrators, sterilization service providers, etc., (all of which are generally referred to as administrators) to have an Internet-based administrator portal 200 that may be accessed by any network enabled device, such as a mobile phone, computer tablet, laptop computer, and/or desktop computer. The Internet-based portal may be in the form of a webpage, a progressive web application, a desktop/laptop/tablet-based application, a mobile device-based application, or otherwise. In general, the driver and the user may be used interchangeably. Data from the administrator portal 200 may be downloaded or otherwise viewed in any suitable manner and/or changed by the driver portal 100. Data from the sterilization process may be uploaded in any suitable manner to the administrator portal 200. Further, images from an imaging device that includes a time stamp each time that the driver services a vehicle is preferably also captured, saved, and made available upon request.

The administrator portal 200 may include a register module 210. The register module 210 permits the administrators to register with the system, preferably with a combination of a user name 212 and a password 214 and their role as an administrator (e.g., Uber fleet manager, Lyft fleet manager, Taxi Fleet manager, sterilization provider, etc.). The registration also preferably includes the administrator identifying a license plate 216 in which the administrator is responsible for that necessitated the use of the system. The registration also preferably includes the administrator identifying a vehicle identification number 218 in which the administrator is responsible for that necessitated the use of the system. For example, the license plate and/or vehicle identification number may be entered for each vehicle that the particular administrator desires to track the sterilization thereof. The administrator portal 200 may provide to the administrator suitable data and options based upon the license plates and/or vehicle identification numbers selected. In this manner, the administrator portal may be customized to the particular needs of the particular administrator.

The administrator portal 200 may include a login module 220. The login module 220 permits the administrator to log into the system, preferably using the combination of a user name 222 and a password 224 the administrator selected as a result of their use of the register module 210. The administrator, based upon their status as an administrator, is permitted to access portions of the system and not permitted to access other portions of the system.

The administrator portal 200 may include a reset password module 228. The reset password module 228 permits the administrator to reset their password to use the system. Preferably, the system requires the administrator to enter their user name, in which a two-factor authentication is used to reset the password, such as a text message, phone call, or e-mail message.

The administrator portal 200 may include an appointment management module 230. The appointment management module 230 may provide an interface for listing previous and future sterilization appointments 232, an interface for adding additional sterilization appointments 233, an interface for editing existing sterilization appointments 234, and an interface for removing existing sterilization appointments 235. For example, the appointments may be a sterilization that has been or to be performed at a car cash, or otherwise. The appointments may be modified by any driver and/or administrator with access to the administrator portal 200. When an appointment is added, removed, and/or edited, the changes are reflected within the appointments module 140 of the driver portal 100. When an appointment is added, removed, and/or edited in the driver portal 100, the changes are reflected within the appointment management module 230 of the administrator portal 200. In addition, when an appointment is added, removed, and/or edited, a communication, such as in the form of a phone call, text message, or e-mail may be automatically sent to the driver and/or administrator based upon their contact information. The system may automatically send reminders to the driver and/or administrator, such as in the form of a phone call, text message, or e-mail, before a sterilization appointment. For example, the reminders may be sent 14 days, 7 days, and 1 day before an appointment. This reminder system ensures that the driver is aware of the sterilization appointments and also creates a record of the driver being reminded of the sterilization appointment.

The administrator portal 200 may include a vehicle management module 240. The vehicle management module 240 may provide an interface for listing vehicles 242 that a particular administrator has a relationship with, an interface for adding additional vehicles 243, an interface for editing existing vehicles 244, and an interface for removing existing vehicles 245. The vehicle management module 240 may provide an interface for adding comments 246 to document any activities that may be desired later for reference. In addition, the comments 246 provides the capability of different entities to share information about a particular driver and/or vehicle. The system may automatically send a welcome message to the driver, such as in the form of a phone call, text message, or e-mail, when the new driver is added to the system. This also notifies the new driver that they have been added to the system. Also, the welcome message preferably includes log-in information so the driver can more easily set up their account in the system. Further, comments may be provided to the driver, and driver comments may be provided to any suitable administrator.

The administrator portal 200 may include a sterilization management module 250. The sterilization management module 250 may include listing of sterilization locations 252 that the vehicle may be sterilized at. The sterilization management module 250 may include an interface for adding additional sterilization locations 253, an interface for editing existing sterilization locations 254, an interface for removing existing sterilization locations 255, and an interface for associating a particular vehicle with a particular sterilization location 256. The system may require a sterilization process to occur, such as within 2 days of the sterilization appointment. In addition, the sterilization management module 250 may be used to schedule an appointment for sterilization service 257. The sterilization management system 250 may also be used to set up driver alerts 258 to notify the driver of the need to set up an appointment 259 for sterilization service.

The administrator portal 200 may include an invoicing module 260. The invoicing module 260 permits the administrator to create invoices, send invoices to drivers and others, and check whether particular invoices have been paid. Also, the system may indicate that the sterilization process is overdue if one or more invoices are past due, so that in this manner the fleet manager and/or potential passengers may be notified that the vehicle is not suitably sterilized.

Figure 3:
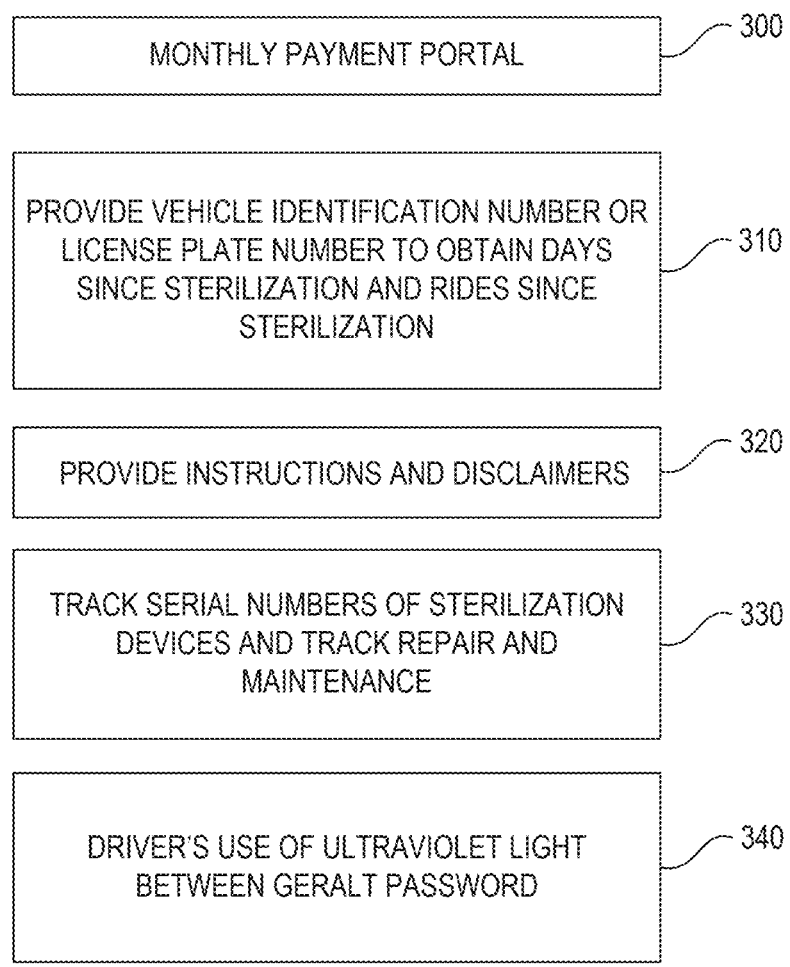
FIG. 3 illustrates portions of a sterilization system.

Referring to FIG. 3, the system may include a monthly payment portal 300 that configures an automatic monthly, or otherwise recurring, payment to be made by the driver to maintain access to the system and derive benefits therefrom. The monthly payment may further include a limited number of sterilization processes, if desired. The payment may be automatically provided to a third-party financial account, if desired.

Figure 4:
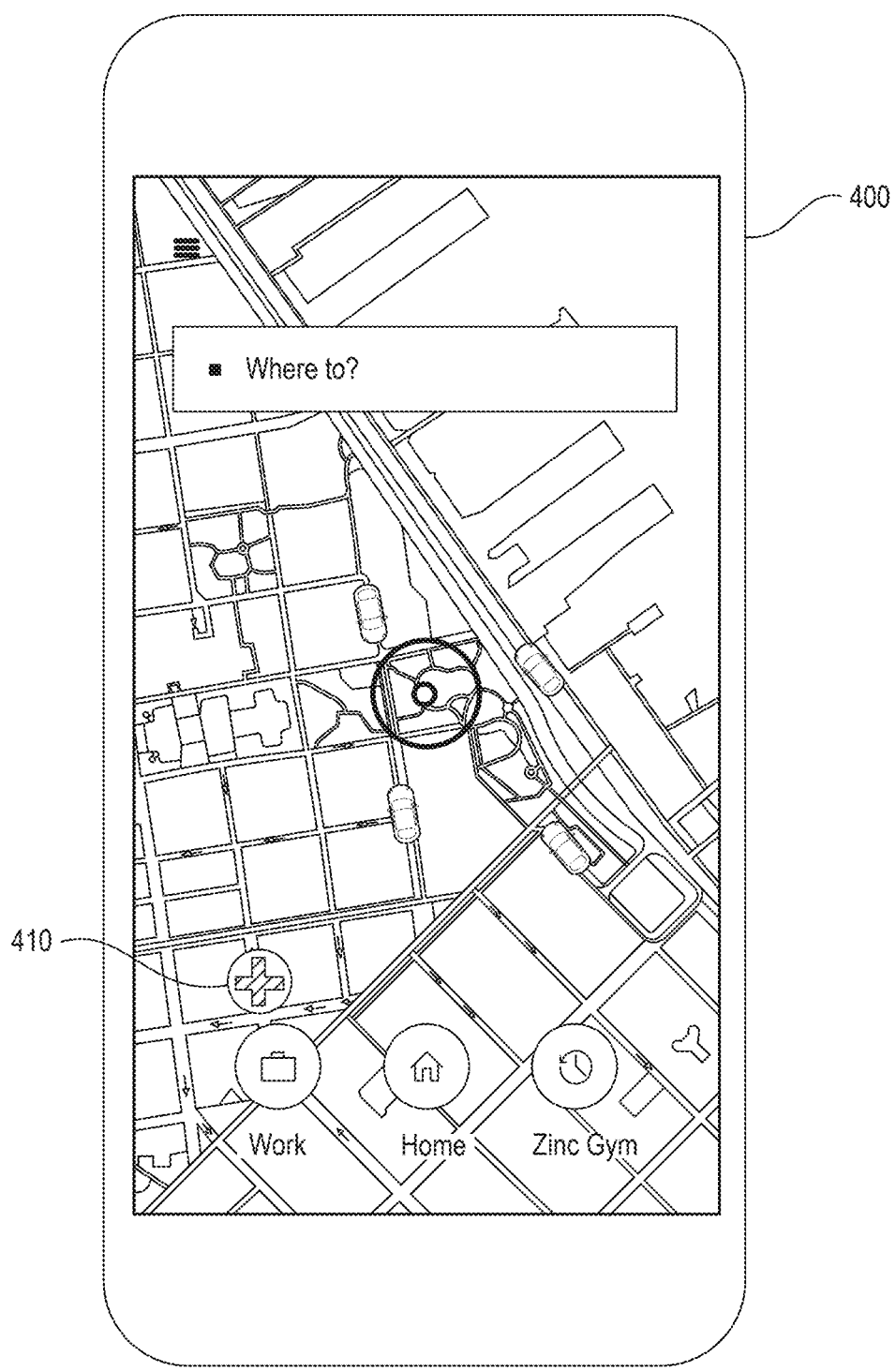
FIG. 4 illustrates an interface on a mobile device with a sterilization button.

Referring to FIG. 4, when the potential passenger is requesting a vehicle, such as using a fleet management system like Uber, the mobile device 400 (e.g., an iPhone) may display a "Sanitized" button 410 on the display. When the "Sanitized" button 410 is highlighted, it preferably indicates that the potential passenger is only requesting a vehicle that has been properly sanitized within a predetermined time period, as determined by the system or otherwise. For example, the system preferably only shows available vehicles that are properly sanitized when the "Sanitized" button 410 is highlighted. For example, the system preferably shows all available vehicles, whether sanitized or not, when the "Sanitized" button 410 is not highlighted. Other settings may likewise be used to indicate the preferences of the potential rider based upon the sanitized status of the vehicle.

Referring again to FIG. 5, the potential passenger and/or administrator (through the administrator portal 200) may be presented with the duration since the last ozone shock sterilization and/or UV sterilization service occurred for the vehicle. By way of example, this may be presented prior to the potential passenger selecting a particular vehicle, such as the number of days that have elapsed 500, since the last sterilization service and/or the number of passengers 510 since the last sanitization service. This provides relevant information that may be of particular value to a potential passenger of a vehicle.

Referring again to FIG. 3, the potential passenger and/or driver and/or administrator may access a sterilization portal 310, such as an application on a mobile phone, or other computing device to look up how long it has been since the last sterilization service has occurred and/or the number of passengers since the last sterilization service has occurred based upon a suitable search criteria, such as a vehicle identification number and/or a license plate number. The number of days may be automatically determined based upon data provided to a network-based computing system from a sterilization device. The number of passengers may be determined by accessing the database of activity of the feet management service(s) being used for that vehicle or otherwise determined in any manner.

Figure 6:
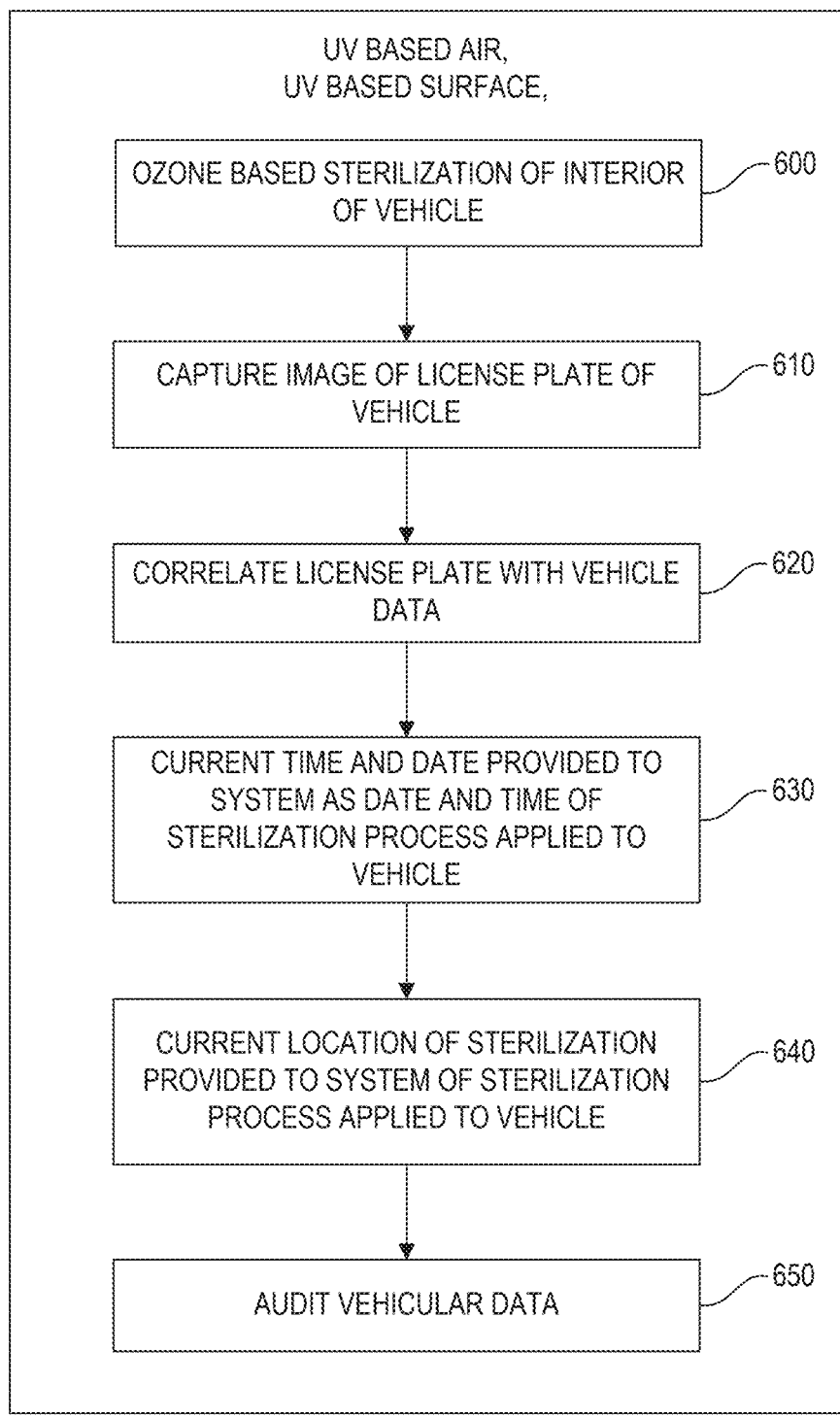
FIG. 6 illustrates a sterilization process.

Referring to FIG. 6, an ozone shock-based sterilization process may be used to provide a sterilization of the interior of the vehicle 600. An ultra-violet (UV) (including UV-C) interior-based sterilization process may be used to provide a sterilization for the surfaces of the interior of the vehicle 600. An ultra-violet (UV) interior-based sterilization process may be used to provide a sterilization for the surfaces and/or the air, inclusive of odors, of the interior of the vehicle 600. The driver may identify themselves by logging into the sterilization process or otherwise the sterilization process may capture an image of the license plate (or vehicle identification number) which identifies the vehicle 610. The system may use image processing to identify the numbers and letters of the license plate (or vehicle identification number) and correlate the identified license plate to vehicular data (or vehicle identification number), based upon the license plate (or vehicle identification number), in the system for the driver 620. The current time and date of the sterilization process is provided to the system, such as cloud-based server, as the latest date and time that the sterilization process has been applied to the vehicle 630. The current time and date of each ozone shock sterilization process and/or the UV sterilization process (inclusive of surfaces and/or air) may also be provided in the form of time and date stamped images captured by the imaging device. The current location of the sterilization process being applied to a vehicle is provided to the system 640. In this manner, the system may track the use of the sterilization process, the time, date, and location of the sterilization process, the duration of the sterilization process, a captured image of the license plate of the vehicle used for the sterilization process at the location of the sterilization process, so that an audit 650 may be performed of the sterilization history to ensure proper sterilization has occurred. In the event of an audit of the tracked data determines that a violation occurred, such as a driver did not proper perform one of the sterilization processes properly the system may automatically generate a violation report that is provided to the system administrator and/or the driver and/or potential passengers.

Figure 5:
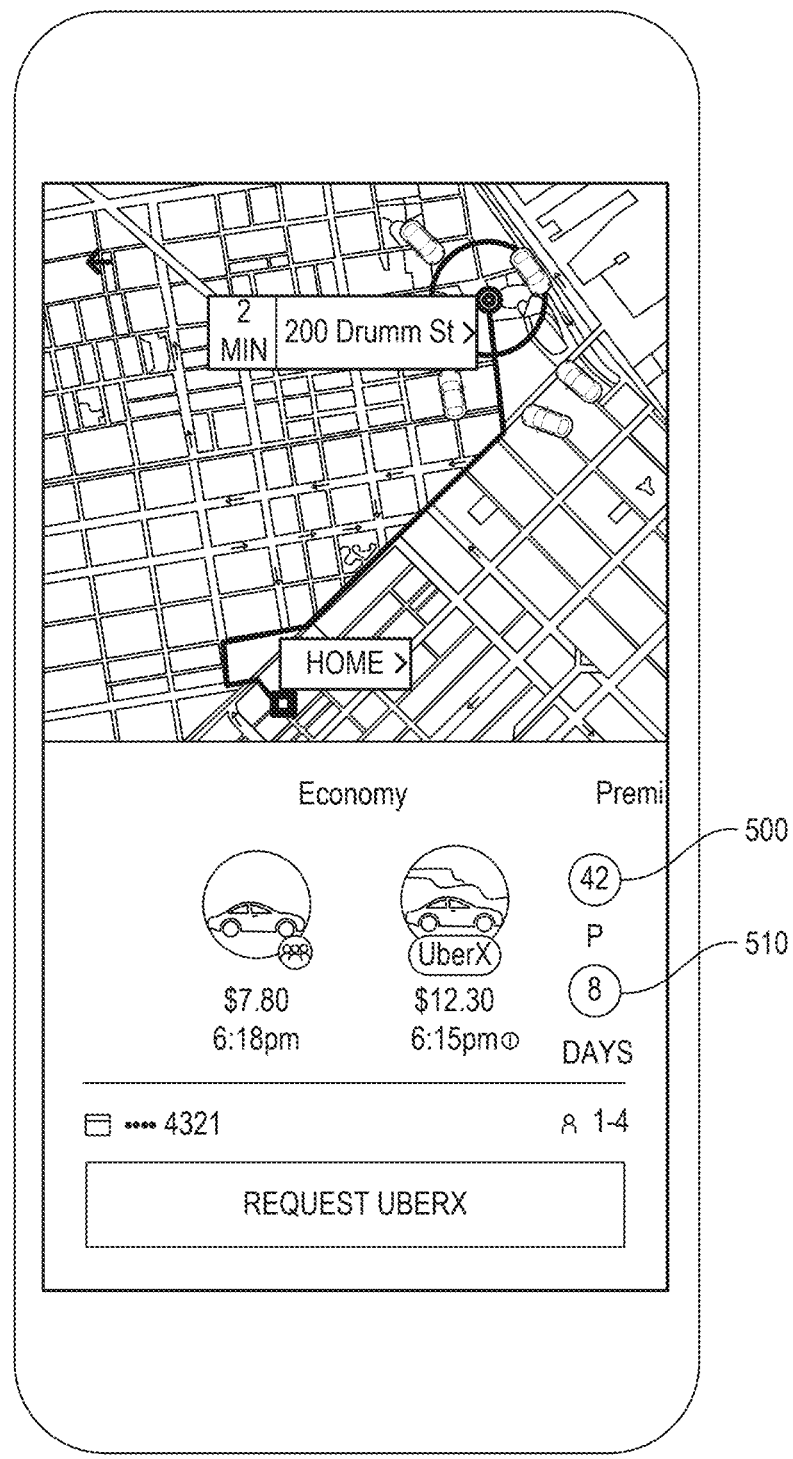
FIG. 5 illustrates an interface on a mobile device with sterilization statistics.

While the application illustrated in FIG. 4 and FIG. 5 is representative of an ozone shock-based sterilization process and/or a UV sterilization process, preferably the driver also uses a portable ultraviolet (e.g., 100 to 400 nm wavelengths) light applied to the interior surfaces of the vehicle and/or the interior air of the vehicle between transporting each of the passengers 340. Preferably, the driver uses the portable ultraviolet light between transporting each of the passengers to reduce the accumulation of viruses, bacteria, fungi, or other microorganisms. The use of the portable ultraviolet light may be interconnected to the system, such as providing for a serial number of the device, a date, a time, a location, and a duration of the use of the ultraviolet light. For example, the fleet management system may manage the trip for a particular passenger, then the fleet management system may require the driver to use the portable ultraviolet light for a predetermined period of time, prior to permitting the driver to pick up an additional passenger. For example, the fleet management system may manage the trip for a particular passenger, then the fleet management system may require the driver to use the portable ultraviolet light for a predetermined period of time, or otherwise the system may not permit the "Sanitized" button 410 to be effective for the driver or otherwise indicating in some manner that the vehicle has not received the ultraviolet light for a predetermined period of time. Further, the driver may use the system to indicate that the portable UV light was applied to the surfaces and/or the air to provide sterilized air after the passenger exited the vehicle and before the next passenger enters the vehicle. In this manner, customers and/or administrators may be made aware of the UV status (inclusive of surfaces and/or air) of the vehicle, such as through the mobile application in the same manner as the ozone shock.

Referring again to FIG. 3, the system may provide instructions and a disclaimer that are presented to a driver, both of which may be required to be viewed and/or accepted prior to using the sterilization process 320. By way of example, the sterilization process may include an ozone sterilizer, sterilized air using ultraviolet light, an ultraviolet sterilizer gun fixed to a sterilizer tower, a portable ultraviolet sterilizer, and/or an emergency clean up unit. Also, a potential passenger may view materials regarding the sterilization process and the manner of looking up the status of any particular vehicle, inclusive of video content, through the system.

The system should further track the serial numbers of the sterilization devices for inventory purposes together with any repair and maintenance for each of the sterilization devices 330. In this manner, the administrator, drivers, and/or potential passengers may determine the likelihood of proper maintenance of the sterilization devices. The serial numbers may be further used to track the replacement of filters, track the cleaning of ozone plates, track the service of the sterilization devices, track the cleaning of the sterilization devices, and track damage reports associated with the sterilization devices. The system may likewise send out service notices, such as by e-mail, text message, or otherwise, if the service is not performed in a timely manner. Further, the system may automatically reorder filters and other parts and inventory that may require replacement or restocking, which are then installed or restocked by a service technician. When the service technician installs replacements or restocks the storage tower, imaging devices may capture images of the activity for tracking purposes.

Figure 7:
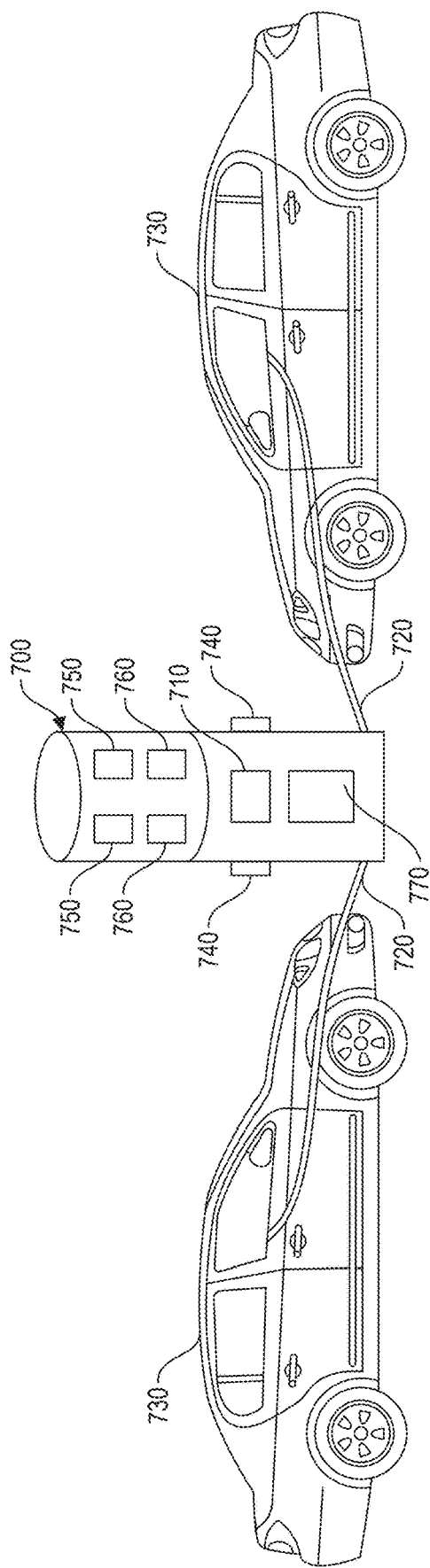
FIG. 7, FIG. 7A, FIG. 7B illustrate a sterilization tower and one or more vehicles.
Figure 7A:
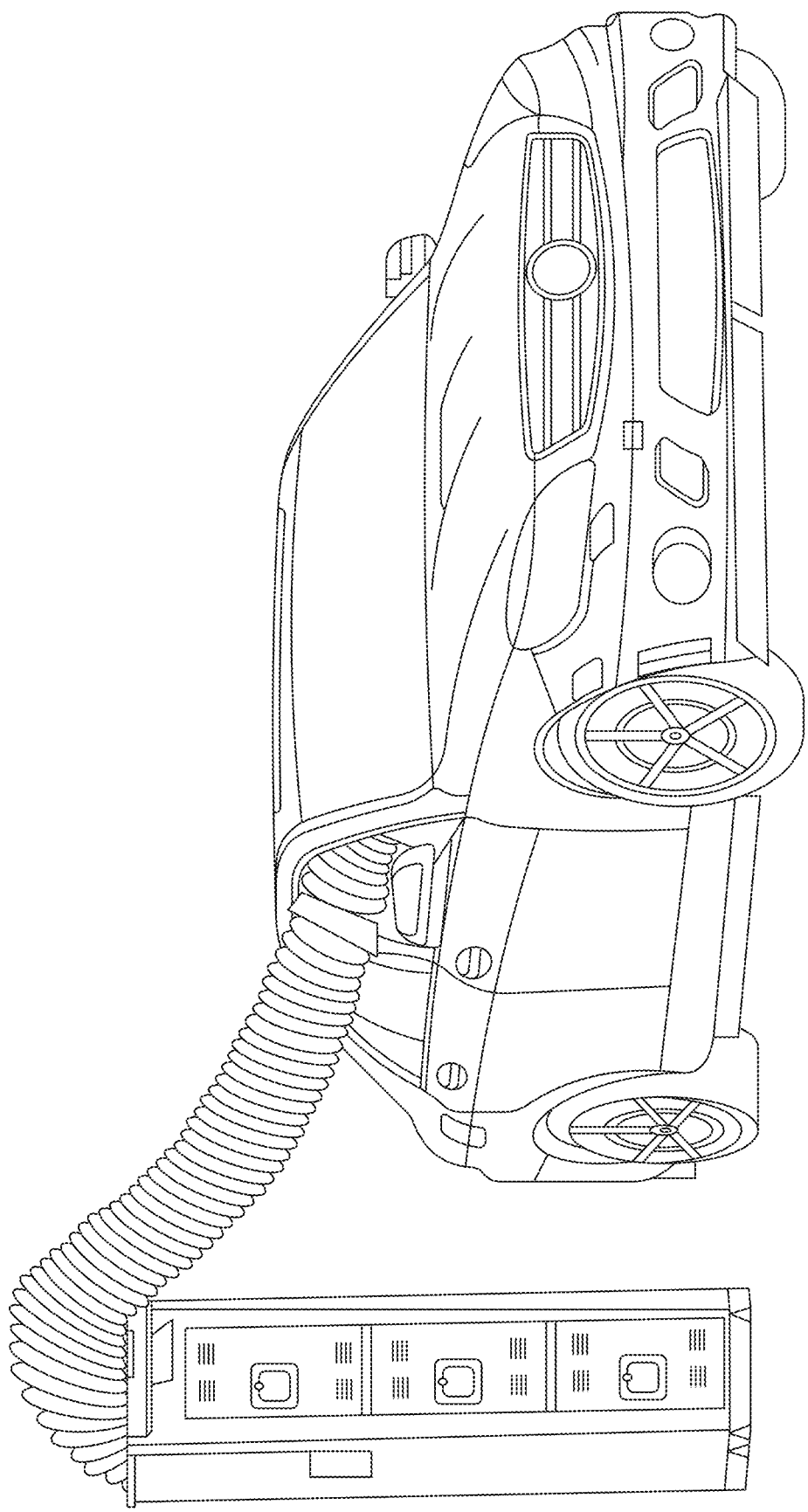
Figure 7B:
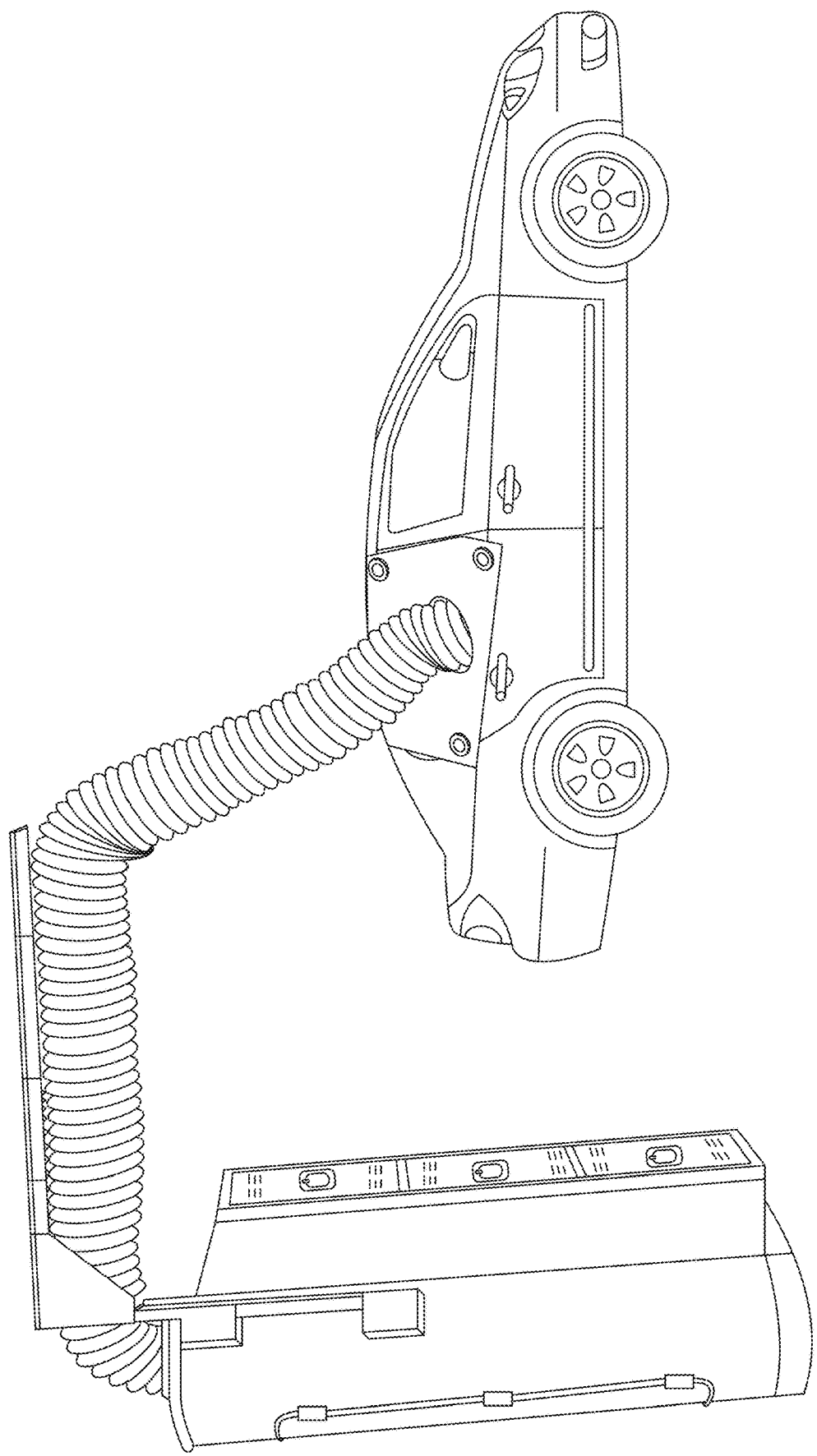

Referring to FIG. 7, FIG. 7A, and FIG. 7B, a vehicle sterilization device 700 may be provided that includes a software application running on an electronic computing device. The software application may include an interface 710 that is used by a user to control the sterilization device. The vehicle sterilization device may also be controlled by an Internet connected program, such as a network-based server and/or a mobile device running an application. Preferably, the driver uses an application on their mobile phone to access and control the vehicle sterilization device 700, which also logs the activity performed, as described herein. The driver may use the application on their mobile phone to confirm the vehicle and/or license plate number. The vehicle sterilization device 700 also preferably includes a pair of imaging devices 740 to capture an image of a respective license plates of vehicles 730 when the vehicle sterilization device 700 is being used. In this manner, there is a high reliability that the vehicle sterilization device 700 is being used by the identified vehicle for the driver, which is preferably used for auditing purposes. In the case that the driver has multiple vehicles, this will permit the system to more readily distinguish between the multiple vehicles. Also, if the vehicle has no front license plate, then the vehicle is turned around so that a rear license plate is visible. Also, if the vehicle has no rear license plate, then the vehicle is turned around so that a front license plate is visible. Moreover, the system may include a lock out from being operated if a license plate is not detected by the respective imaging device 740. The vehicle sterilization device 700 may include a respective pair of lights 750, one for each vehicle 730, that indicate that the vehicle sterilization device 700 is in use or otherwise the vehicle is identified. Preferably, the respective light 750 flashes when the corresponding vehicle is being sterilized or otherwise the vehicle is identified. The vehicle sterilization device 700 may include a respective speaker 760 that provides instructions on how to properly use the vehicle sterilization device 700 for the driver. In this manner, the likelihood of using the vehicle sterilization device 700 in an improper manner is reduced. The components of the sterilization device may be housed within a single container, such as a stainless steel metal cylinder. However, other embodiments may include the components being separated from one another in multiple housings. The components of the system may include, for example, one or more high-volume fans, one or more ozone-producing devices, a UV sterilization light for air, a suction and/or blowing fan (e.g., 2,400 CFM), one or more portable UV sterilization light for surfaces, a carbon filter, etc., described in more detail later. The sterilization device may also include one or more tubular hoses 720 for transferring ozone to the interior of a respective vehicle 730 and for removing ozone from the interior of the respective vehicle 730. In another embodiment, the sterilization device may also include a different hose (or the same hose) for providing UV sterilized air to the interior of a respective vehicle and/or for removing sterilized air from the interior of a respective vehicle, at a time during which the system is not providing and/or removing ozone from a respective vehicle since UV sterilized air tends to neutralize the ozone. In another embodiment, UV sterilized air may be provided (preferably at a time when the system is not providing and/or removing ozone from a respective vehicle) using an interior sterilized UV air source, as described later. The end of the hose is inserted into the vehicle, such as through a window, such as illustrated FIG. 7A and/or FIG. 7B.

If desired, a driver may sign up for a monthly service membership that permits them to periodically use the vehicle sterilization device 700. Also, as part of the monthly service membership the driver should also agree to use the ultraviolet light on the interior of the vehicle, such as the heavily touched areas of the interior of the vehicle, on a regular basis such as after every passenger, or otherwise to provide air that is exposed to ultraviolet light being circulated within the interior of the vehicle using a fan. As a result of signing up for such a monthly service membership, the driver may be provided with a conformance sticker that may be affixed to the vehicle so that passengers may readily obverse it (see FIG. 8). Further, the conformance sticker may include a serial number, or otherwise the vehicle identification number, or otherwise the license plate number, that may be used by the potential passenger to confirm the current sterilization status of the vehicle by looking it up in the system. The conformance sticker may be mailed to the driver, if desired.

By using a vertical tower 700, that is preferably affixed to the ground, all of the equipment to perform the vehicle sterilization may be included therein. Using the vertical tower 700 permits the use of a relatively large ozone generator, such as an ozone generator that provides between 20,000 mg/hour to 60,000 mg/hour which is an effective amount to sterilize a vehicle within a relatively short period of time. Using the vertical tower 700 permits the use of a relatively large charcoal sterilizer, such as a charcoal scrubber that consumes 2,500 cubic feet/minute or more which is an effective amount remove the air within a relatively short period of time based upon the use of a fan. The vertical tower 700 may further include an additional UV sterilization light that provides sterilized air when the ozone is not being provided and/or removed, which is provided to the interior of the vehicle using the fan and the hose. In another embodiment, UV sterilized air may be provided (preferably at a time when the system is not providing and/or removing ozone from a respective vehicle) using an interior sterilized UV air source, as described later. The tubular hoses 720 are preferably 8 inches to 12 inches in diameter or more and extend from the vertical tower 700 to the respective vehicle 730, being inserted within a window. During operation, the ozone is pumped in high volumes into the vehicle so that the sterilization is performed in a timely manner (e.g., 5 to 15 minutes, preferably dependent on the size, interior volume, and/or type of vehicle), the ozone is stopped, and the air evacuation is automatically turned on to remove the ozone from the vehicle to a safe level relatively fast (e.g., 1 to 5 minutes, preferably dependent on the size, interior volume, and/or type of vehicle). In some embodiments, UV sterilized air may be provided after the removal of the ozone, if desired. If desired, each vehicle may include a respective profile that is looked up based upon the imaging of the license plane. The profile may have data determined by the system based upon the type of vehicle, such as the volume contained therein, or determined by the driver and/or the administrator. The profile may define the duration and/or level of the ozone generation being provided to the vehicle, and the duration and/or the level of the air evacuation to remove ozone from the vehicle, and/or the duration and/or level of UV sterilized air being provided to the vehicle at a different time. The profile may include the current time and date of each ozone shock sterilization process and/or UV sterilized air in the form of time and date stamped images captured by the imaging device, and more preferably the latest such time date stamped image. In this manner, a customized sterilization process may be achieved. The profile may define the duration and/or level of the portable UV light provided to the surfaces of the vehicle, if desired.

The vertical tower 700 may include a locked door 770 that is unlocked by the interface, unlocked by the mobile application, or otherwise unlocked as a result of imaging the license place and identifying the vehicle in the system. Once the door is unlocked, the driver may access the respective hose, initiate the ozone generation process and/or initiate the air sterilization process. The ozone generation process and/or UV based air sterilization process, and/or the air evacuation process are preferably performed in a sequential manner by the vertical tower, in an automated manner not requiring more than the user initiating the process. The vertical tower 700 may further include a mobile ultraviolet light which may be accessed by unlocking the door 770 which is used to perform additional sterilization of the vehicle. The use of the vertical tower 700 is especially applicable for drivers that do not have ultraviolet-based sterilizer for the interior of their vehicle, inclusive of drivers that do not have respective profile on the system.

Referring also to FIG. 9, FIG. 9A, FIG. 9B, FIG. 9C, FIG. 9D, a hose 900 is connected at one end to a high-volume fan 910. The other end of the hose 900 is constructed to be placed on or in a vehicle so that ozone and/or UV sterilized air can transfer from the system to the vehicle during the sanitization process, then remove the ozone and/or UV sterilized air from the vehicle during the evacuation process. On the side of the high-volume fan 910 opposite the hose 900, are located one or more ozone-generating devices 920. These ozone-generating devices 920 are placed within the cylinder so that air flows from the ozone-generating device 920, through the high-volume fan 910, then into the hose 900 to the vehicle. Positioned on the other side of the ozone-generating devices 920, in some embodiments, is a second high-volume fan 930. This second high-volume fan 930 blows air onto or into the ozone-generating devices 920 during sterilization process, then reverses direction and pulls air away from the ozone-generating devices during an evacuation process. Further upstream, on the opposite side of the second high-volume fan 930, is a carbon filter assembly 940. The carbon filter assembly 940 comprises one or more carbon filters that are designed to remove ozone during an evacuation process. The system may also include a UV light generator that is selectively enabled, such as when the ozone is not being produced and/or evacuated, to provide sterilized air to a destination, such as a vehicle.

In one embodiment, the vertical tower may operate using two different modes, namely, a sterilization mode and an evacuation mode. During the sterilization mode ozone or UV sterilized air, but preferably not both at the same time, is produced and then transferred by the fans through the hose into the vehicle. Sterilization of the vehicle can take 5 to 10 minutes, preferably dependent on the size, interior volume, and/or type of vehicle. After the sterilization process is complete, the vertical tower automatically changes to operate in the evacuation mode. The evacuation mode removes ozone or sterilized air, if present, from the vehicle and passes the removed ozone over the carbon filter assembly to remove the ozone from the air, typically 1 to 5 minutes, preferably dependent on the size, interior volume, and/or type of vehicle. In the evacuation mode the fans that caused the ozone and/or UV sterilized air to enter the vehicle may operate in reverse, or alternatively, there may be one or more additional fans that are designed to move air from the vehicle that are activated only during this mode.

The high-volume fans may include a cubic feet per minute rating of 2500 or more so they can move 20,000 mg/hour to 60,000 mg/hour or more of ozone or UV sterilized air into a vehicle during the sterilization mode. During the evacuation mode, at least one fan causes the removal of ozone or UV sterilized air from the vehicle at a rate of up to 2500 cubic feet per minute or more. In addition, there may be multiple different sizes of towers, such as small, medium, and large. For example, the large ozone tower may include a cubic feet per minute rating of 2500 or more. For example, the medium tower may include a cubic feet per minute rating of 1500 or more. For example, the small tower may include a cubic feet per minute rating of 800 or more.

The carbon filter assembly 940 is constructed so that ozone being removed from the vehicle passes through the carbon filter assembly before exiting the system. The fan that operates to remove the ozone is preferably constructed so that it is adjacent to the carbon filter assembly. The carbon filter assembly preferably includes multiple carbon filters, although any other filter type that is capable of filtering out ozone may be used.

The vertical tower may include an electronics housing 750 that houses the electronics to operate the device and interconnect with the Internet and/or Wi-Fi and/or Bluetooth and/or mobile devices and/or computing devices. The electronics housing 750 may also include an interface, such an operator interface, so that a driver may use the system to perform the ozone sterilization process alone or in combination with their computing device.

The vertical tower may include a locker 760 that includes a portable ultraviolet sterilizer, which is preferably interconnected to the vertical tower 700, either using a cable or a wireless interconnection, so that the usage of the ultraviolet portable sterilizer may be logged by the system and associated with the particular driver and/or vehicle. In particular, the portable UV sterilizer provided in the tower is useful for drivers that do not have a UV sterilizer in their vehicles for the surfaces in the interior of the vehicle and/or the air in the interior of the vehicle.

In other embodiments, one or more vertical towers (with or without the hose) may be used to provide ozone sterilization and/or UV air sterilization to the interior of buildings, theaters, large indoor enclosed areas, ski resorts, ski lifts, small indoor enclosed areas. For example, during a first time period (such as a predetermined scheduled time period), such as the daytime, the tower may provide UV sterilized air to the area. This assists with sterilizing the environment and the air within the environment so that it is safer for those in the area. For example, during a second time period (such as a predetermined scheduled time period), such as the nighttime, the tower may provide ozone air to the area. After a sufficient duration, the tower may evacuate the air from the area to remove the ozone. This assists with sterilizing the environment and the air within the environment so that it is safer for those that subsequently return to the area. This may be done on a schedule, if desired. If desired, the ozone and/or the UV evacuation may be vented to the exterior of the area, or not vented to the exterior of the area, as desired. Preferably, the ozone evacuation is designed to reduce the levels to below 1% ozone level by volume. One or more sensors may likewise be incorporated into the device and/or environment that sense the ozone levels and the evacuation continues until the level is reduced to 1% ozone or less by volume.

Figure 10:
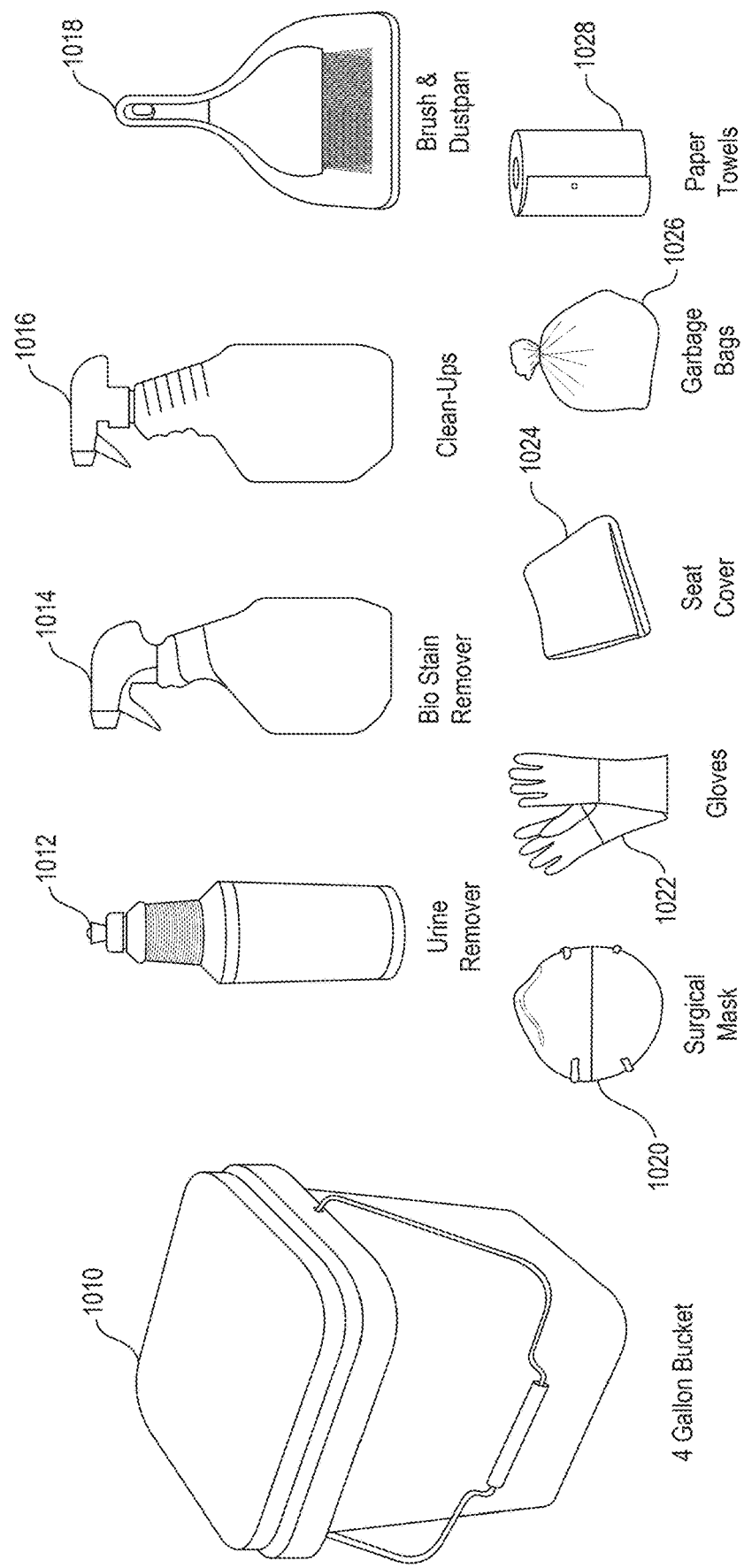
FIG. 10 illustrates a cleaning kit.

Referring to FIG. 10, the vertical tower 700 may include a cleanup kit 1000 that is available to drivers to clean up their vehicle or otherwise purchase. The cleanup kit 1000 may include several different types of cleaning supplies. For example, the cleanup kit 1000 may include a bucket, such as a 4-gallon bucket 1010. For example, the cleanup kit 1000 may include a bottle of urine remover 1012. For example, the cleanup kit 1000 may include a bottle of bio stain remover 1014. For example, the cleanup kit 1000 may include a bottle of cleaner 1016. For example, the cleanup kit 1000 may include a brush and dustpan 1018. For example, the cleanup kit 1000 may include surgical mask(s) 1020. For example, the cleanup kit 1000 may include gloves 1022. For example, the cleanup kit 1000 may include a seat cover 1024. For example, the cleanup kit 1000 may include garbage bags 1026. For example, the cleanup kit 1000 may include paper towels 1028. The collection of products are selected to take care of most emergencies on the road with respect to cleaning.

Figure 11A:
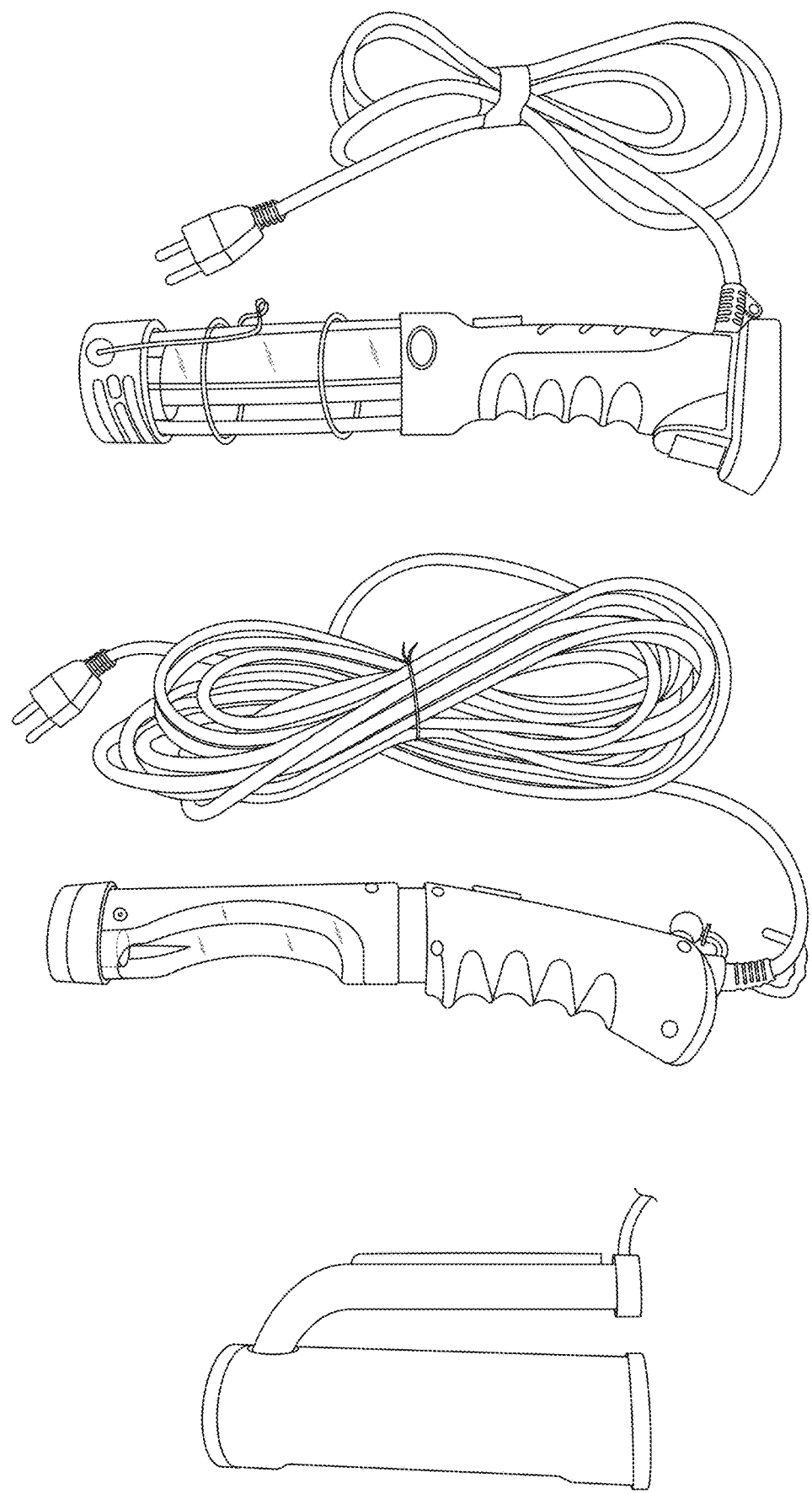
FIG. 11A and FIG. 11B illustrate an ultraviolet light.
Figure 11B:
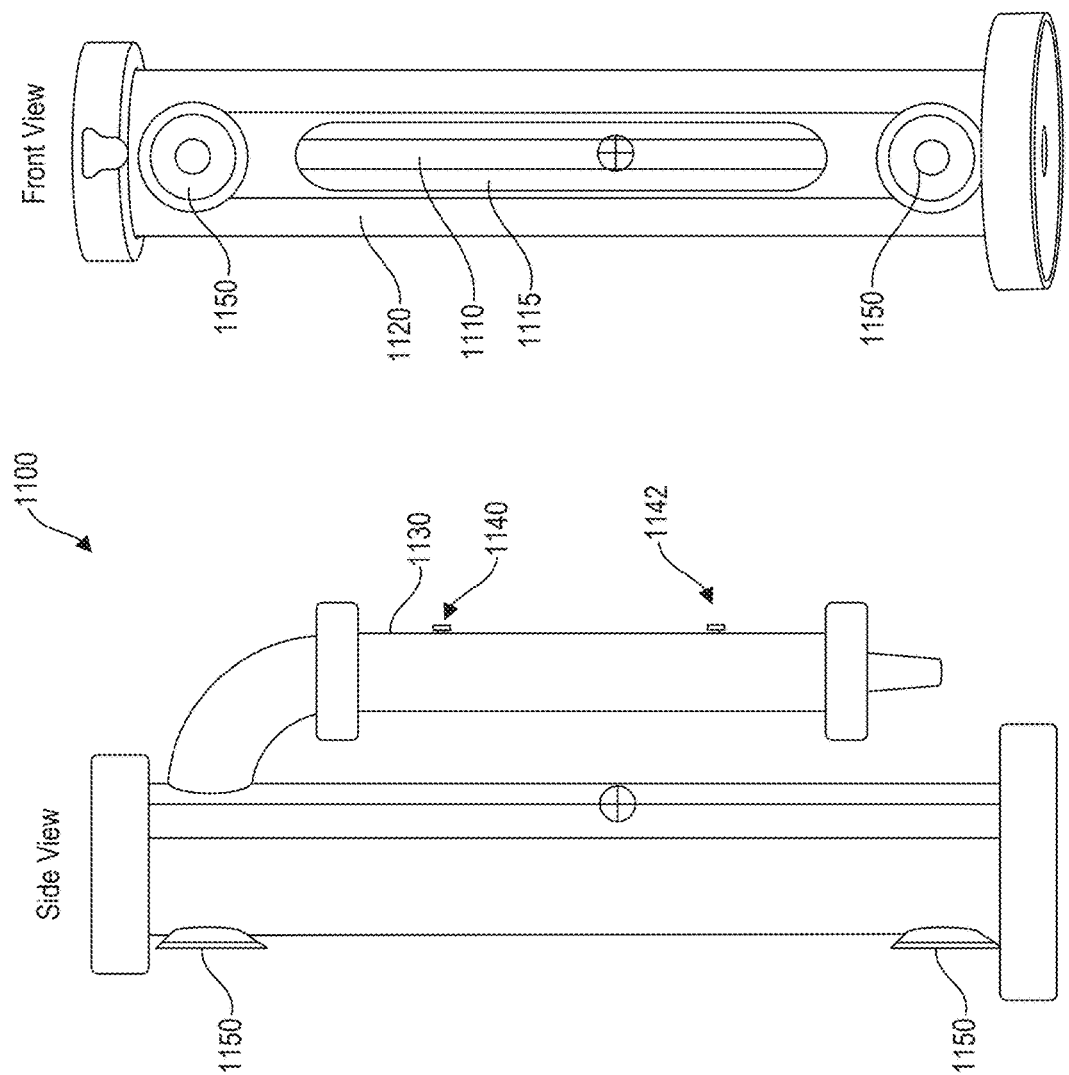

Referring to FIG. 11A, FIG. 11B, exemplary portable ultraviolet sterilizers 1100 are illustrated. In one embodiment, an ultraviolet light 1110 is recessed into a housing 1120, so that the ultraviolet light 1110 is protected against being damaged during use. The ultraviolet light 1110 may be surrounded by a reflective surface 1115 so that additional light is directed outwardly. A handle 1130 of the ultraviolet sterilizer 1100 optionally includes a pair of on/off switches 1140, 1142 that are spaced apart from one another, such as approximately 5 inches. When pressed, each of the switches 1140, 1142 is in an 'on' position, and when no longer pressed, each of the switches 1140, 1142 is in an 'off' position. The switches 1140, 1142 are spaced apart in such a manner that the palm of the hand presses against one of the switches 1140, 1142 as the user grips the handle 1130. The switches 1140, 1142 are spaced apart in such a manner that the thumb of the hand presses against the other one of the switches 1140, 1142. Both switches 1140, 1142 need to be engaged to turn on the ultraviolet sterilizer, and only one switch 1140, 1142 needs to be disengaged to turn off the ultraviolet sterilizer. With the pair of spaced apart switches 1140, 1142 on the handle 1130, it is difficult for the user to bend their wrist toward themselves in a manner that the ultraviolet light directly shines in their eyes. The ultraviolet light is normally of sufficiently low power that the user looking directly at the ultraviolet light does not immediately hurt their eyes. However, several hours later the damage to the eyes from looking at the ultraviolet light tends to become apparent. To reduce the likelihood that the user directly views the ultraviolet light 1110, one or more high powered light emitting diodes 1150 that primarily illuminate in the visible light spectrum are included. The ultraviolet light 1110 and the light emitting diodes 1150 are oriented so that they both direct light in generally the same direction when the switches are both on. The high-powered light emitting diodes 1150, which are uncomfortable for the user to view, tends to reduce the likelihood that the user will directly view the ultraviolet light thereby reducing the likelihood of damaging their eyes. Also, the light emitting diodes illuminate the area being sterilized to simplify the use by the user. The ultraviolet sterilizer 1100 may be battery powered, plugged into a USB plug in a vehicle, plugged into a cigarette lighter plug in a vehicle, or otherwise plugged into wall power (e.g., 110 volts). The ultraviolet sterilizer 1100 may be wirelessly interconnected to the system, such as the user's mobile phone, so that the usage of the ultraviolet sterilizer may be tracked by the system, including the date, the time, the location, and the duration of usage.

Figure 12:
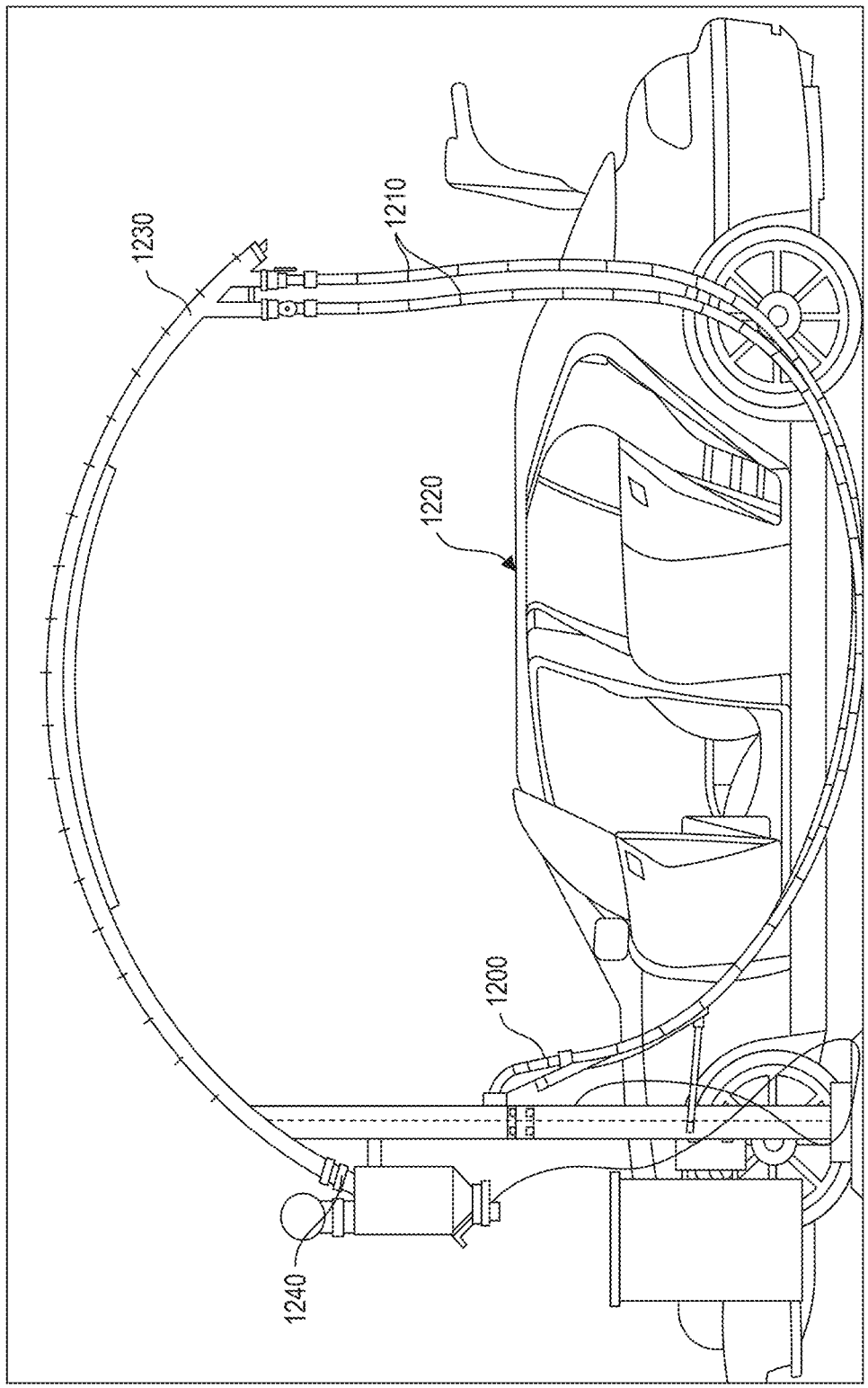
FIG. 12 illustrates an ultraviolet light on the end of an arc.

Referring to FIG. 12, in another embodiment one or more ultraviolet lights 1200 may be interconnected to the end of relatively long powered connector(s) 1210, which may include a vacuum line for a vacuum system to clean the vehicle 1220. The relatively long powered connector(s) 1210, may be interconnected to an arched structured 1230 that is rotatable around an axis 1240. The ultraviolet lights 1200 are inserted within the interior of the vehicle for the sterilization process. The arched structure 1230 is movable from one side of the vehicle 1220 to the other side of the vehicle 1220, by rotation thereof, so that sterilizing the vehicle 1220 using the one or more ultraviolet lights 1200 is simplified. In addition, the vacuum system of FIG. 12 may include the same or a different tubular hose and associated ozone sterilization and/or UV air sterilization to provide sterilization to the interior of the vehicle, and subsequent evacuation of the ozone and/or sterilized air from the interior of the vehicle.

Figure 13:
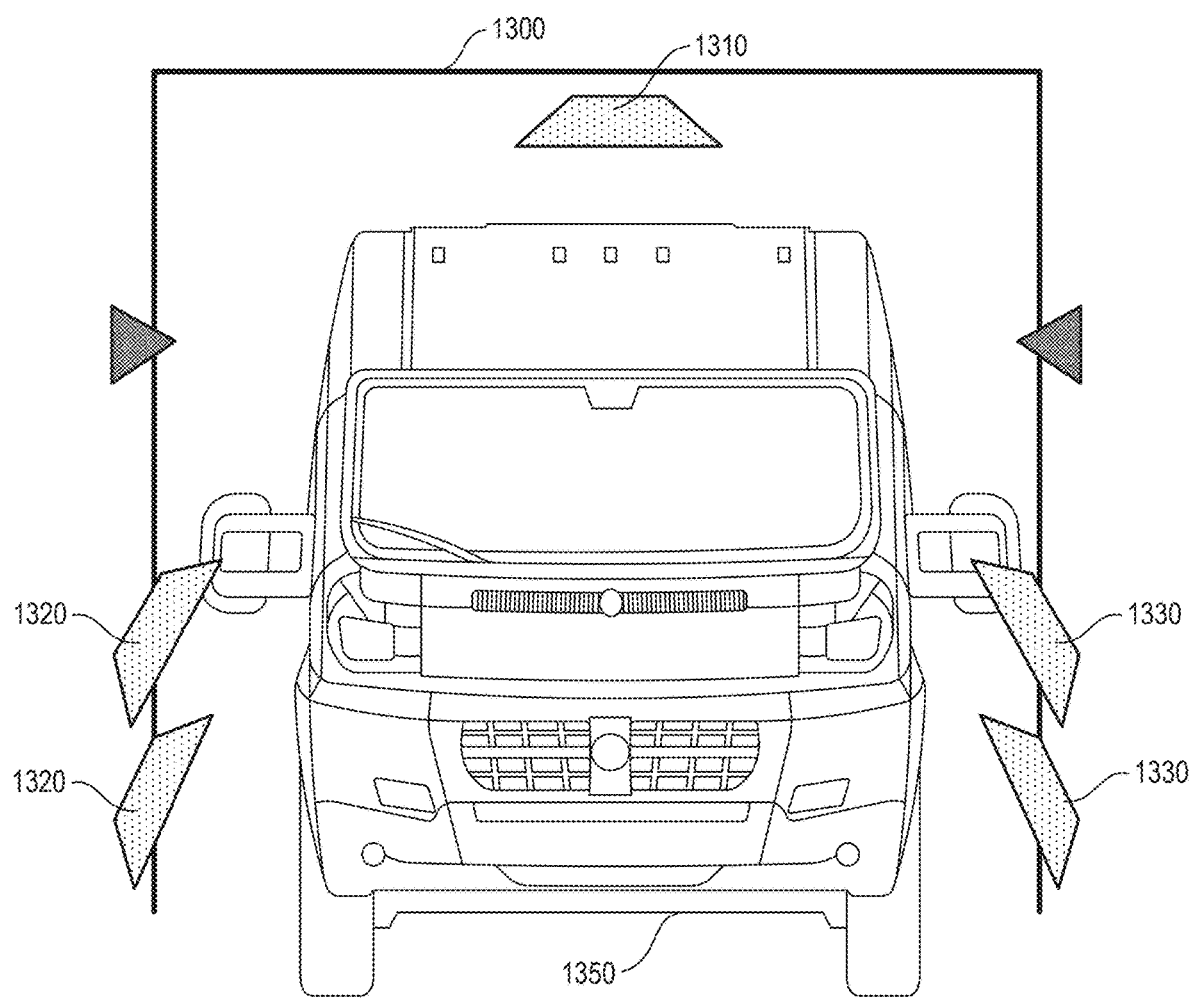
FIG. 13 illustrates ultraviolet lights on a frame.
Figure 15:
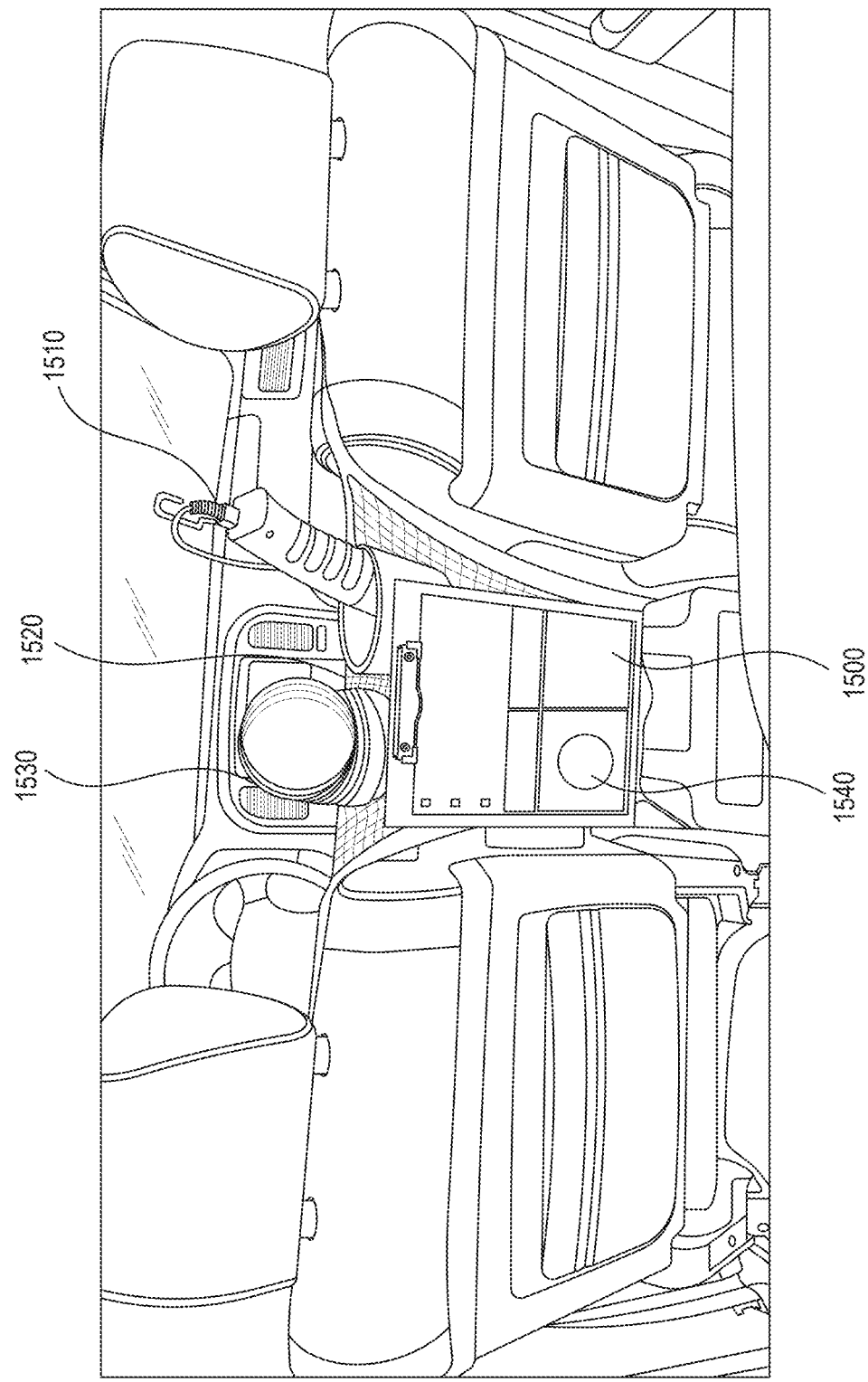
FIG. 15, FIG. 15A, FIG. 15B, FIG. 15C, illustrate a sterilization device within a vehicle.
Figure 15A:
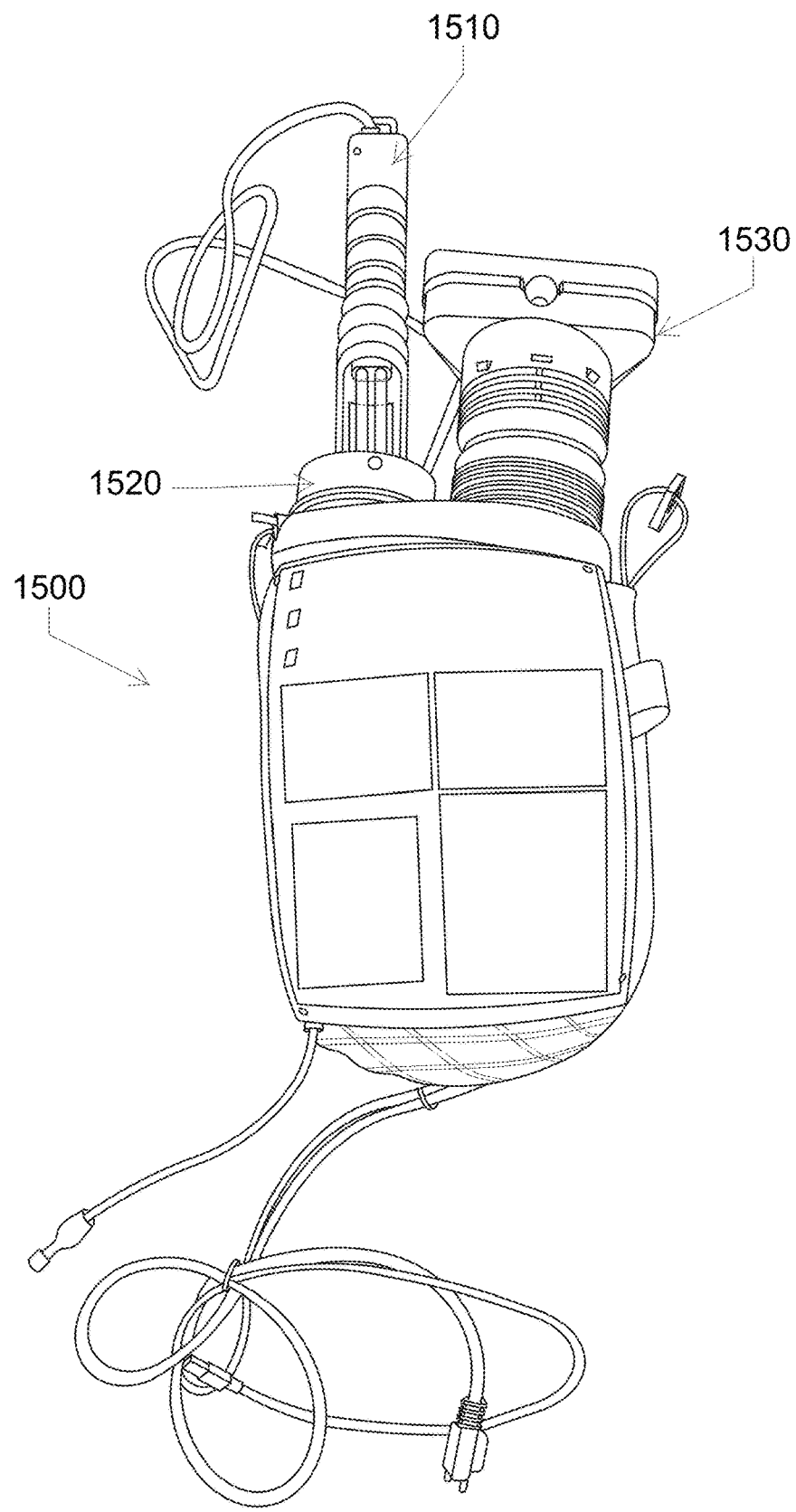
Figure 15B:
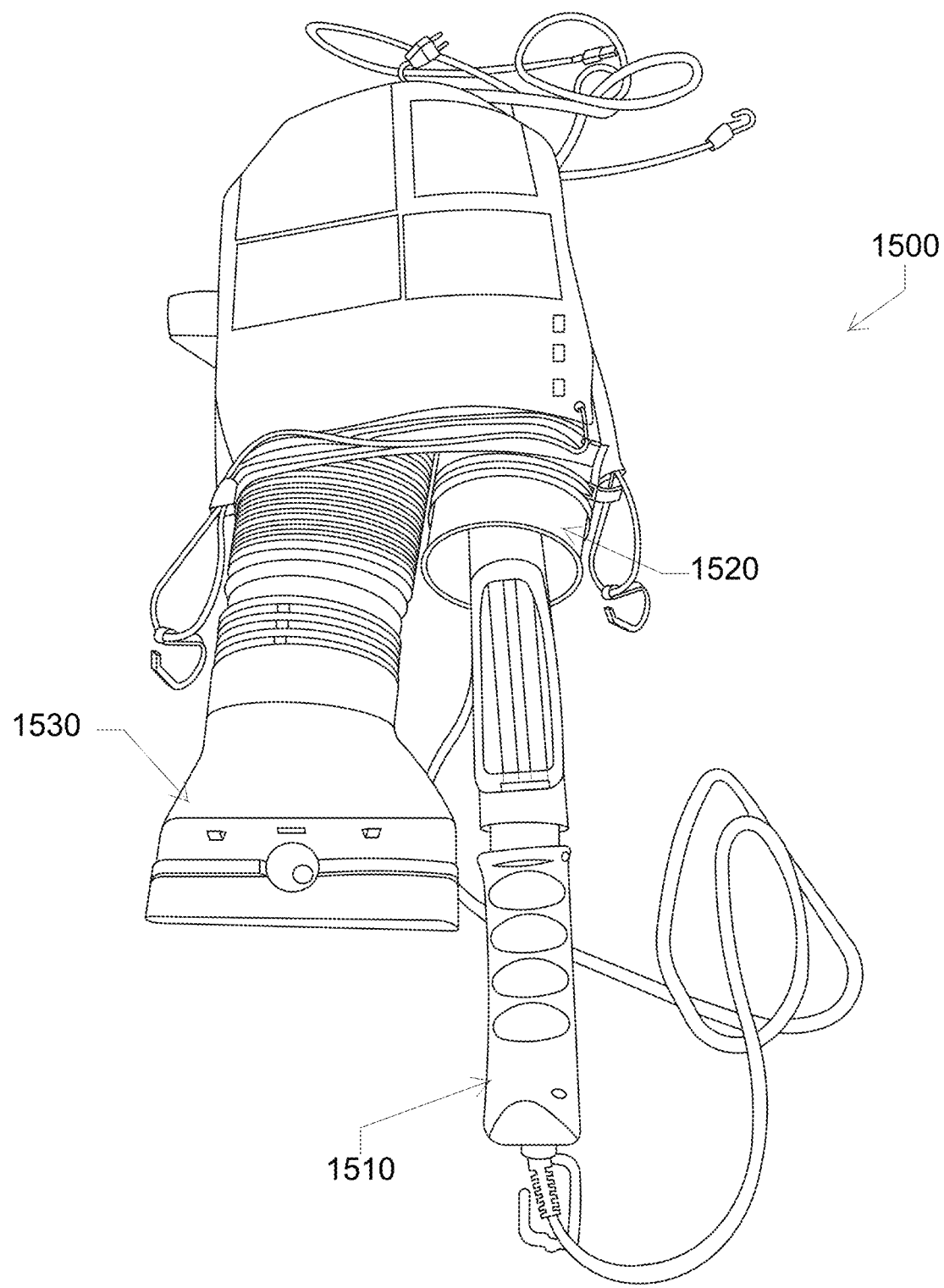
Figure 15C:
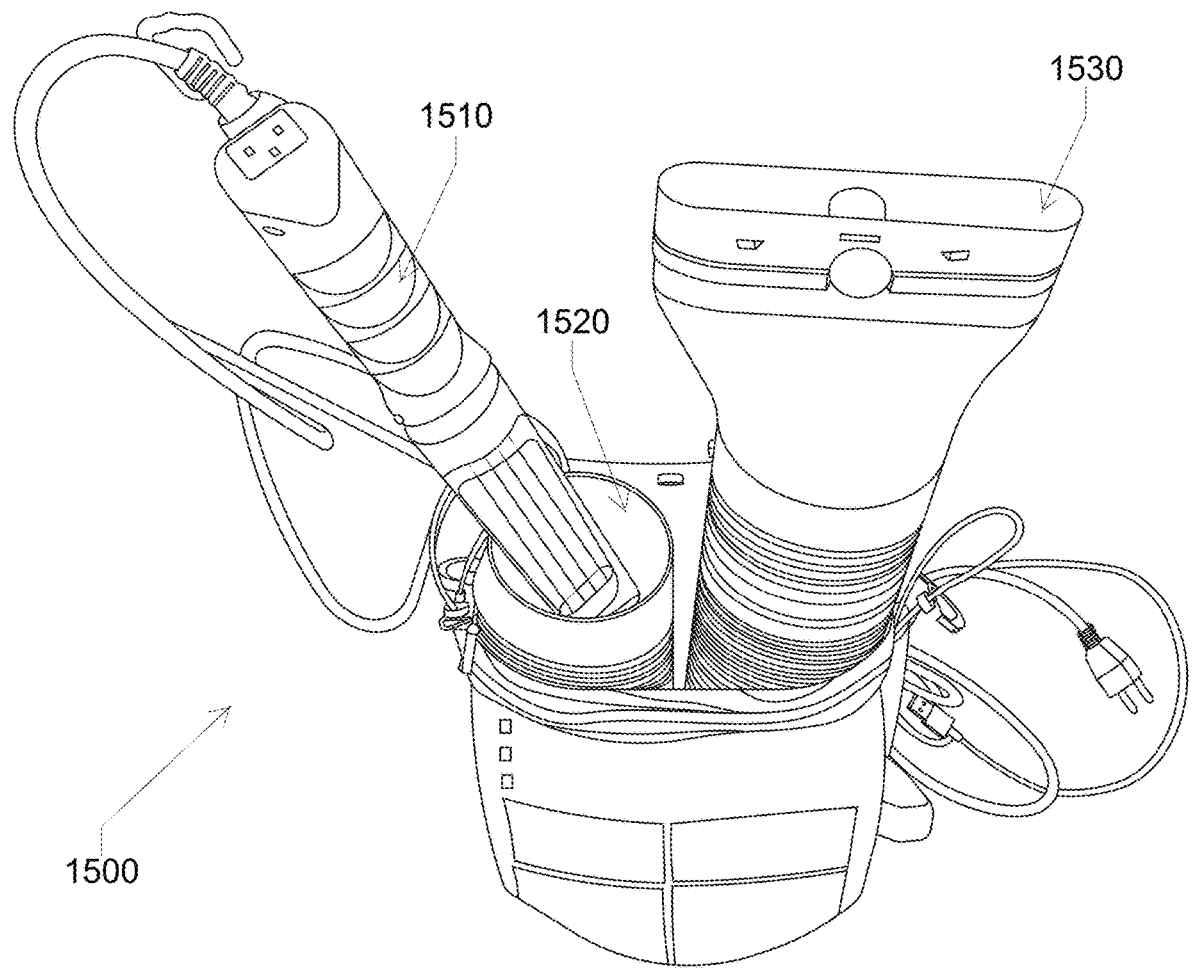

Referring to FIG. 13, in another embodiment one or more ultraviolet lights 1310, 1320, 1330 may be interconnected to a frame 1300 around the periphery having a spacing suitable for a vehicle 1350. The upper ultraviolet light 1310 sterilizes the upper portion of the vehicle 1350 as the vehicle passes underneath. The left ultraviolet lights 1320 sterilizes the left portion of the vehicle, including that which is within the path of the ultraviolet lights, as the vehicle passes alongside. The right ultraviolet lights 1330 sterilizes the right portion of the vehicle 1350, including that which is within the path of the ultraviolet lights, as the vehicle passes alongside. This facilitates sterilizing the vehicle 1350 as the vehicle passes under a stationary frame 1300. Also, this facilitates sterilizing the vehicle 1350 as the frame 1300 passes over a stationary vehicle 1350. The frame 1300 may be included as part of a multi-stage car wash. Preferably, the driver exits the vehicle, and the sterilizer is passed over the vehicle twice to sterilize the vehicle for a duration of 5 minutes or more. Also, if windows are rolled down, if a sunroof is opened, if a convertible has the top down, the ultraviolet light more readily sterilizes the interior of the vehicle. The frame or other arched structure may also be used to provide sterilization for other surfaces, including for example, helmets, bowling balls, harnesses, go carts, snow tubs, jet skis, and any other sized piece of equipment from small to large.

Referring to FIG. 14, the hose 1400 may include an attachment 1410 that is sized to fit in an opening of the vehicle when a window is rolled down. The attachment 1410 may be expandable to fit the window opening. For example, the attachment may use a set of one or more magnets to retain the attachment to the vehicle to provide a better seal, while being readily detachable without damaging the vehicle.

Referring to FIG. 15, FIG. 15A, FIG. 15B, FIG. 15C, a vehicle may include a sterilization device 1500 positioned between the front seats of the vehicle and secured to the headrest areas. The passenger may take out an ultraviolet handheld sterilizer 1510 from a holder 1520 so that the passenger and/or driver may sterilize the interior surface of the vehicle before they spend much time in the vehicle. The sterilization device 1500 may include an interior blower that blows air that is sterilized with the ultraviolet handheld sterilizer 1510. The sterilization device 1500 may be powered by being inserted into the cigarette lighter. The sterilization device 1500 may be used as a 'wand' to sterilize the surfaces of the interior. While the ultraviolet light is not being used by the passengers and/or driver, the ultraviolet light may be inserted into the holder 1520 to sterilize the air that is being blown out through the air blower 1530 and to remove odors from inside the vehicle (see FIG. 16). In addition, the driver may place a "Viruses Free Zone" sticker 1540 on the sterilization device 1500 to signify their agreement to maintain the sterilization procedures.

Figure 17:
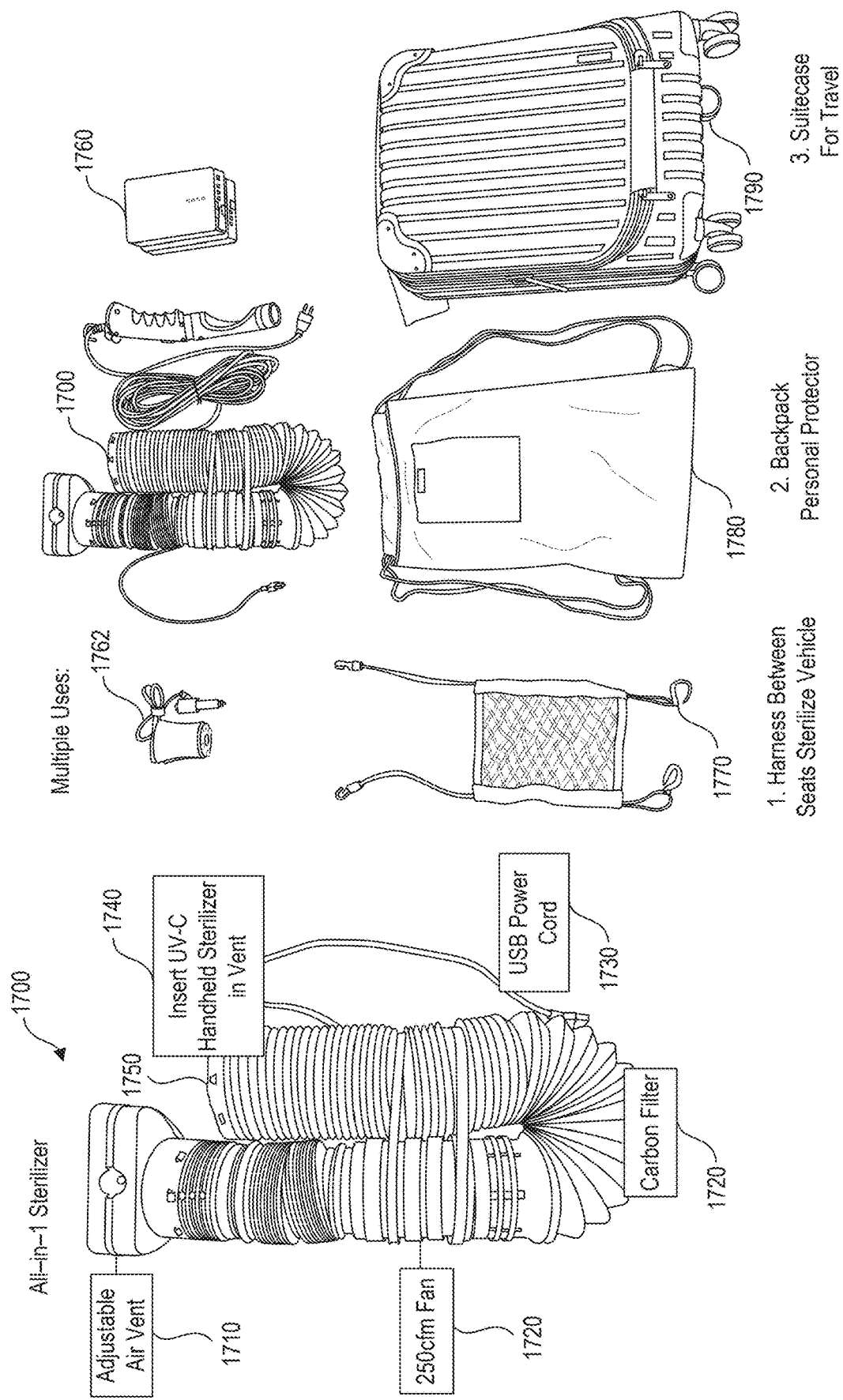
FIG. 17 illustrates an all-in-one sterilization system.

Referring to FIG. 17, an all-in-one sterilizer system 1700 is illustrated. The all-in-one sterilizer system 1700 may include an adjustable air vent 1710. The adjustable air vent 1710 includes an exterior vent together with a hose portion that can be bent in any desirable angle, and which maintains the angle that it is bent to. In this manner, the airflow from the vent 1710 can be directed in a desired direction. The all-in-one sterilizer system 1700 may include an integrated fan unit 1720 that directs air out the adjustable air vent 1710. The all-in-one sterilizer system 1700 includes an integrated carbon filter 1720 to filter the air passing through the all-in-one sterilizer system 1700. The all-in-one sterilizer system 1700 may include a USB power cord 1730 to provide power to operate the fan 1720. A handheld UV sterilizer 1740 may be attached to a long cord that is powered by the USB power cord 1730. The handheld UV sterilizer 1740 may be used to sterilize proximate surfaces to the all-in-one sterilizer system 1700. The handheld UV sterilizer 1740 may be inserted into the intake opening 1750 of the all in-one sterilizer system 1700 to sterilize air that is being blown into the area proximate the all in-one sterilizer system 1700. In some cases, the all-in-one sterilizer system 1700 may be powered by a battery pack 1760 or a car adapter 1762. The all-in-one sterilizer system 1700 may be used in many different environments. In one embodiment, a harness 1770 may be used to support the all-in-one unit between the front seats of a vehicle. In another embodiment, a backpack 1780 may be used to support the all-in-one unit as a unit in a form suitable for being carried around by a user. In another embodiment, a suitcase for travel (e.g., such as a carry-on size for an airplane) 1790 may be used to support the all-in-one unit as a unit in a form suitable for being carried onto an airplane. While on the airplane, the all-in-one sterilizer system 1700 in the suitcase 1790 has the adjustable air vent directed toward themselves while being positioned in front of their seat to blow sterilized air on them to protect against airborne viruses. In addition, one of the all-in-one sterilizer system vents may be interconnected to a face mask worn by a user by using a flexible hose to further ensure that the user only receives sterilized air from the all-in-one sterilizer system, and not potentially harmful air from the environment around the user.

Figure 18:
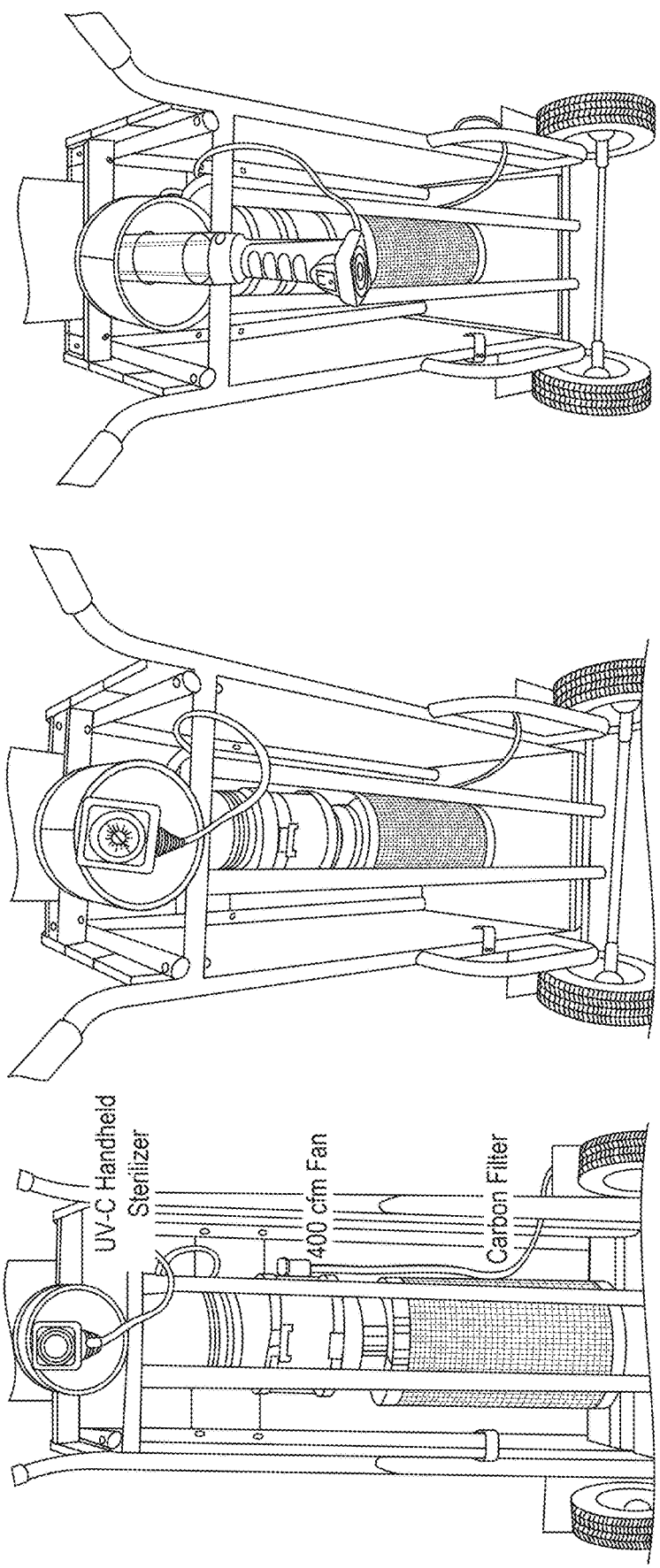
FIG. 18 illustrates another sterilization embodiment.

Referring to FIG. 18, in another embodiment an ultraviolet air sterilizer may include a carbon filter, a fan, an ozone generator, a UV light generator, a portable ultraviolet wand, all of which is on a mobile platform, to provide sterilization to surfaces.

Figure 18A:
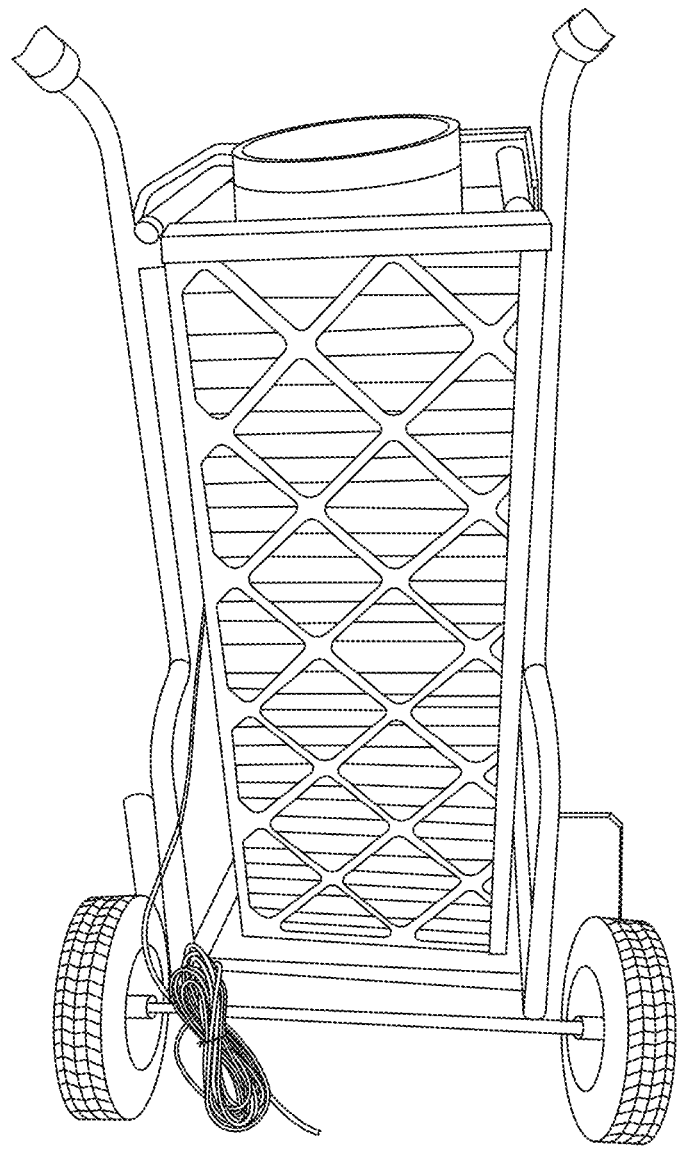
FIG. 18A illustrates another sterilization embodiment.

Referring to FIG. 18A, in another embodiment an ultraviolet air sterilizer may include a detachably connectable filter (e.g., HEPA filter).

By way of example, after every previous passenger the driver and/or the next passenger may make use of the portable UV light sterilization for the surfaces that are likely to be touched by the driver and/or previous passengers. When the next passenger is in the vehicle, the UV handheld sterilizer is preferably inserted into the sterilizer system to sterilize the air inside the vehicle and also to reduce odors within the vehicle. Also, such as weekly, the vehicle is preferably shocked with the tower based ozone sterilization process and/or the tower based UV light sterilization process. Further, such as monthly, the vehicle may receive a 30-day chemical sterilizer shield applicated by an electrostatic spray on the interior surfaces of the vehicle to ensure the vehicle has been sterilized. In this manner, on a regular basis, the vehicle is provided with the ozone sterilization process, the UV air sterilization process, and the chemical sterilization shield process.

Figure 19:
FIG. 19 illustrates a portable sterilization system with a carbon filter.

Referring to FIG. 19, it was determined that for the air sterilization system a carbon based filter should be replaceable so that it may be replaced after extended use. More preferably, the carbon based filter should be readily replaceable and positioned in a location that is readily observable to increase the likelihood that it is periodically replaced for improved performance. A carbon filter assembly 1900 may include internal threads and the corresponding hose may include external threads, with the carbon filter assembly 1900 rotatably secured by engaging the internal threads of the carbon filter assembly 1900 with the external threads of the hose with one another (or the carbon filter assembly 1900 may have external threads and the hose may have internal threads). Other detachable engagements may likewise be used. This is also applicable to the embodiments illustrated in FIG. 9, FIG. 15, FIG. 18, etc.

Figure 20:
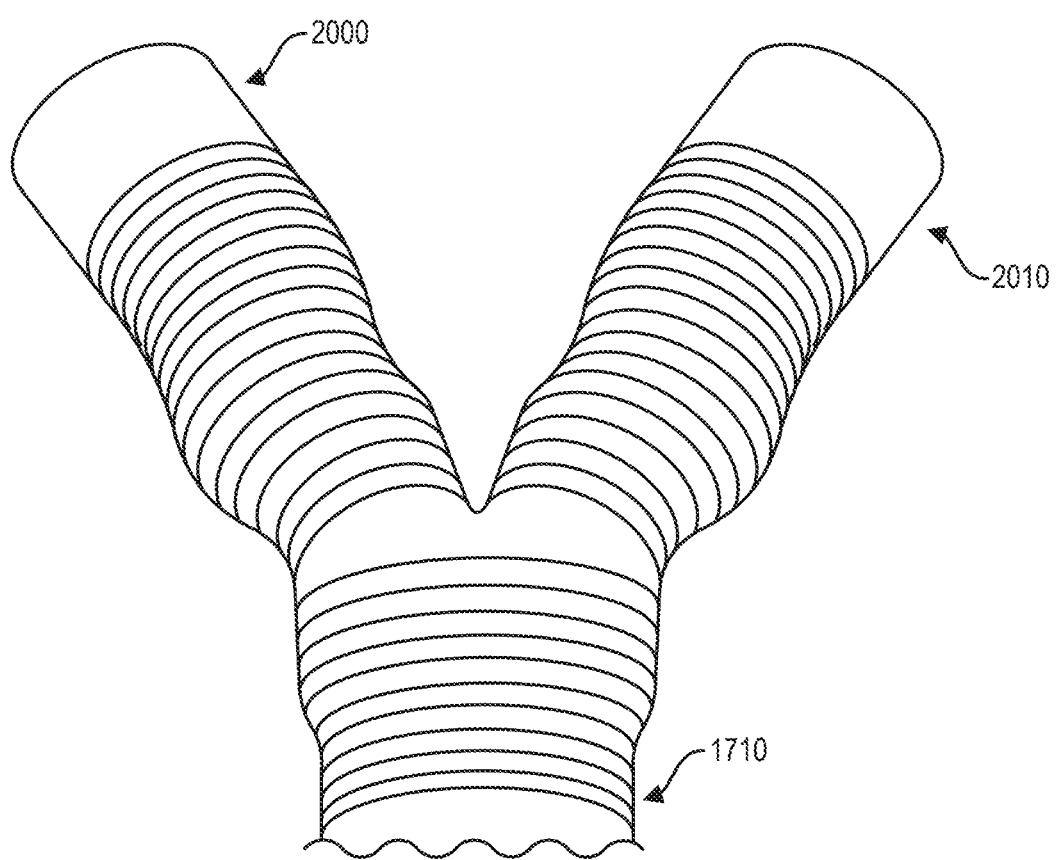
FIG. 20 illustrates a dual vent port for a portable sterilization system.

Referring to FIG. 20, it was determined that for the air sterilization system, there are instances where multiple users each preferably have access to a personalized air flow, while making use of a single air sterilization system. To accommodate multiple users, the adjustable air vent 1720 may include a plurality of vents 2000, 2010. Each of the vents 2000, 2010 may be independently movable and independently aligned in a desired direction by the user. The respective vents maintain the alignments of the respective hose, and is readily movable to different alignments.

In many cases, it is desirable to include additional particle filtration to further provide cleaning for the environment proximate the air sterilization system. The additional particle filtration may include removal from the air flow of over 95%, more preferably over 95%, and more preferably over 99% of particles with a diameter equal to 0.3 micrometers, with the filtration efficiency increasing for particle diameters both less than and greater then 0.3 micrometers. The filter may, for example, be composed of a mat of randomly arranged fibers, such as fiberglass with diameters between 0.2 and 2.0 micrometers. The airspace between filtration fibers is typically much greater than 0.3 micrometers. Unlike sieves or membrane based filters, the filters preferably are designed to target a range of particle sizes that are trapped (stick to a fiber) through a combination of one or more of diffusion, interception, and impaction.

In some cases, it is desirable for the air sterilization system to be included within a vehicle in a manner that is more transparent to the passengers. In this case, it is desirable to integrate the air sterilization system into the seat of the vehicle such that the only portion of the air sterilization system that is visible are the vents and the controls. This provides a reduced profile for the air filtration system.

Figure 21:
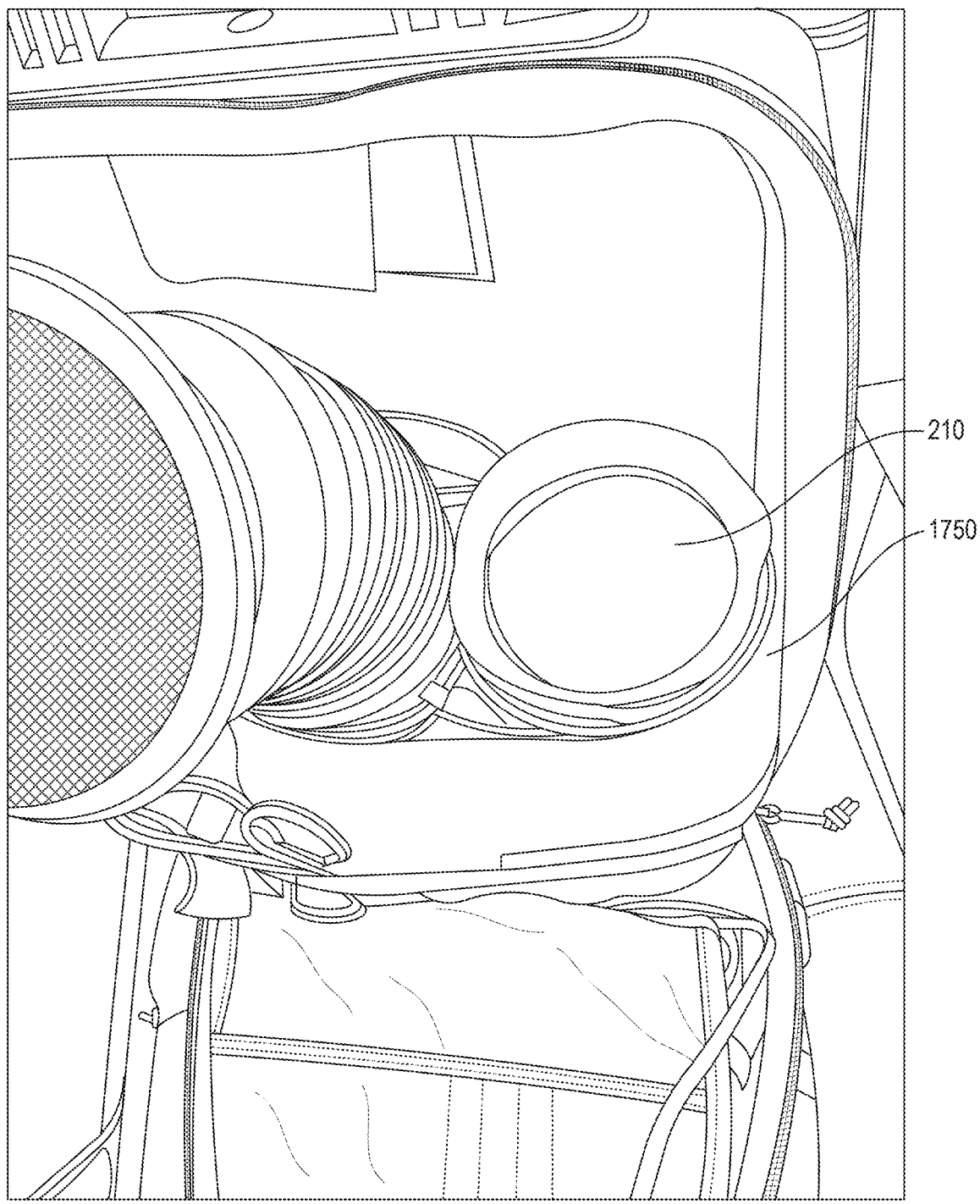
FIG. 21 illustrates a portable sterilization system with a reflective vent.

Referring to FIG. 21, the air sterilization system may include the intake opening 1750 with the interior thereof including a reflective material 2100 therein. The reflective material 2100 preferably encircles the entire interior surface area in 360 degrees. The reflective material 2100 also preferably extends from a location proximate the terminal end of the hose down a substantial length of the interior of the hose. Preferably, the length of the reflective material within the hose is at least as long as the UV light emitting portion of the UV light generator that is inserted therein. In this manner the UV light emitted from the UV light generator has additional dwell time, with the same output levels, to increase the effectiveness of the sterilization of the air.

Figure 22:
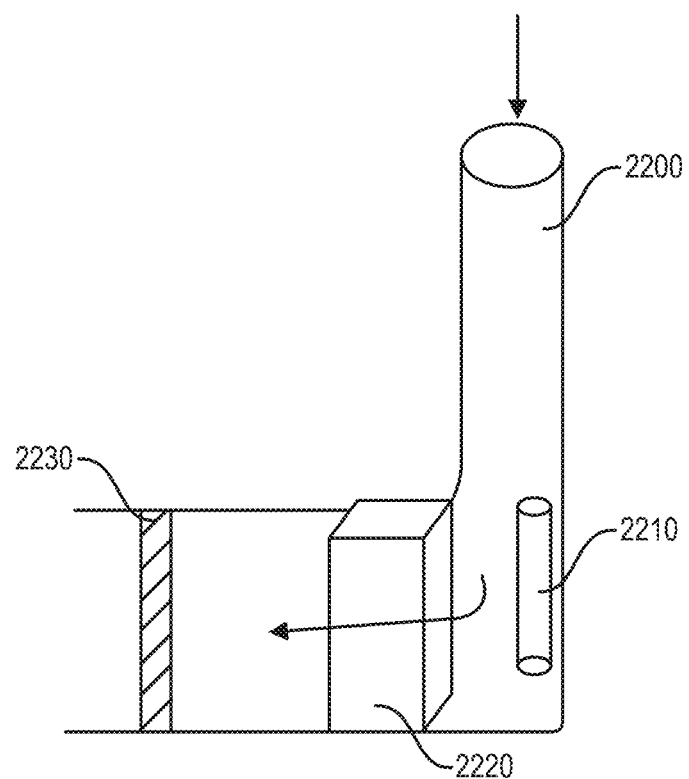
FIG. 22 illustrates a sterilization system with an electronic filter.

Referring to FIG. 22, the air sterilization system may include an air intake 2200 within which is inserted or otherwise included a UV light 2210, which sterilizes the air, especially for viruses. After being sterilized by the UV light 2210, the air may pass through an electronic filter 2220 to reduce viruses and bacteria. The electronic filter 2200 may include, for example, microporous graphene foam using a low-level electric current passing therethrough. Also, a filter 2230, such as the additional particle filtration described above, may be included for additional filtration.

Referring again to FIG. 7, the vertical tower 700 may include in one embodiment the locked door 770 that supports a carbon filter on its inside for air outflow from the vertical tower 700 where the air passes through the carbon filter. The vertical tower 700 may include in another embodiment the locked door 770 that supports a small particle filter on its inside for air outflow from the vertical tower 700 where the air passes through the small particle filter. The vertical tower 700 may include in another embodiment the locked door 770 that supports a UV light source on its inside for air outflow from the vertical tower 700 and/or air inflow to the vertical tower where the air passes within the light emitted by the UV light source.

When air that includes ozone is passed through a carbon filter, the ozone is substantially removed from the air. In contrast, when air is passed through the carbon filter and then ozone is introduced into the air flow, it was determined that residual effects of the carbon filter tends to remove or otherwise neutralize the introduced ozone, thereby reducing the effectiveness of the ozone generation to provide ozone to the environment. If desired, one port of the vertical tower 700 (such as an upper port) may blow out air with ozone that is not filtered by a carbon filter, and another port (such as a door port) may blow out air that does not include substantial ozone and is filtered by a carbon filter.

Figure 23:
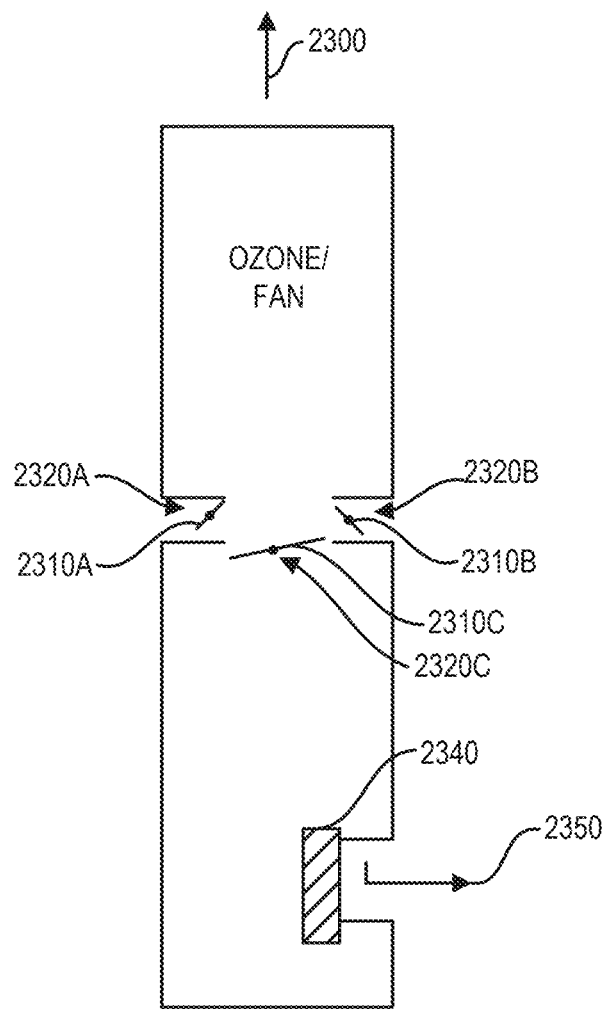
FIG. 23 illustrates a tower system that includes a dual airflow system.

Referring to FIG. 23, the vertical tower may include a first air path where a fan in combination with an ozone source provide an airflow output 2300 that include air with ozone. The vertical tower may include one or more dampers 2310A, 2310B, 2310C (or other selective opening/closing structures) that may selectively open and close a respective passageway for air 2320A, 2320B, 2320C. By opening the dampers 2310A, 2310B and by closing the damper 2310C, the air flows in from the sides of the vertical tower and up through the ozone and fan region to provide the airflow output 2300 that includes ozone in the airflow. By closing the dampers 2310A, 2310B and by opening the damper 2310C, the air flows in from the top of the vertical tower and down through the ozone and fan region, with the ozone generation turned off or otherwise not providing ozone to the airflow, to provide an airflow output 2350 that does not include ozone in the airflow. The airflow output 2350 is preferably filtered by a carbon filter 2340. In this manner, the system provides both air that passes through a carbon filter without ozone, and air that passes through a region that provides ozone without the carbon filter. Accordingly, the carbon filter is selectively included in the path of the air.

Figure 9:
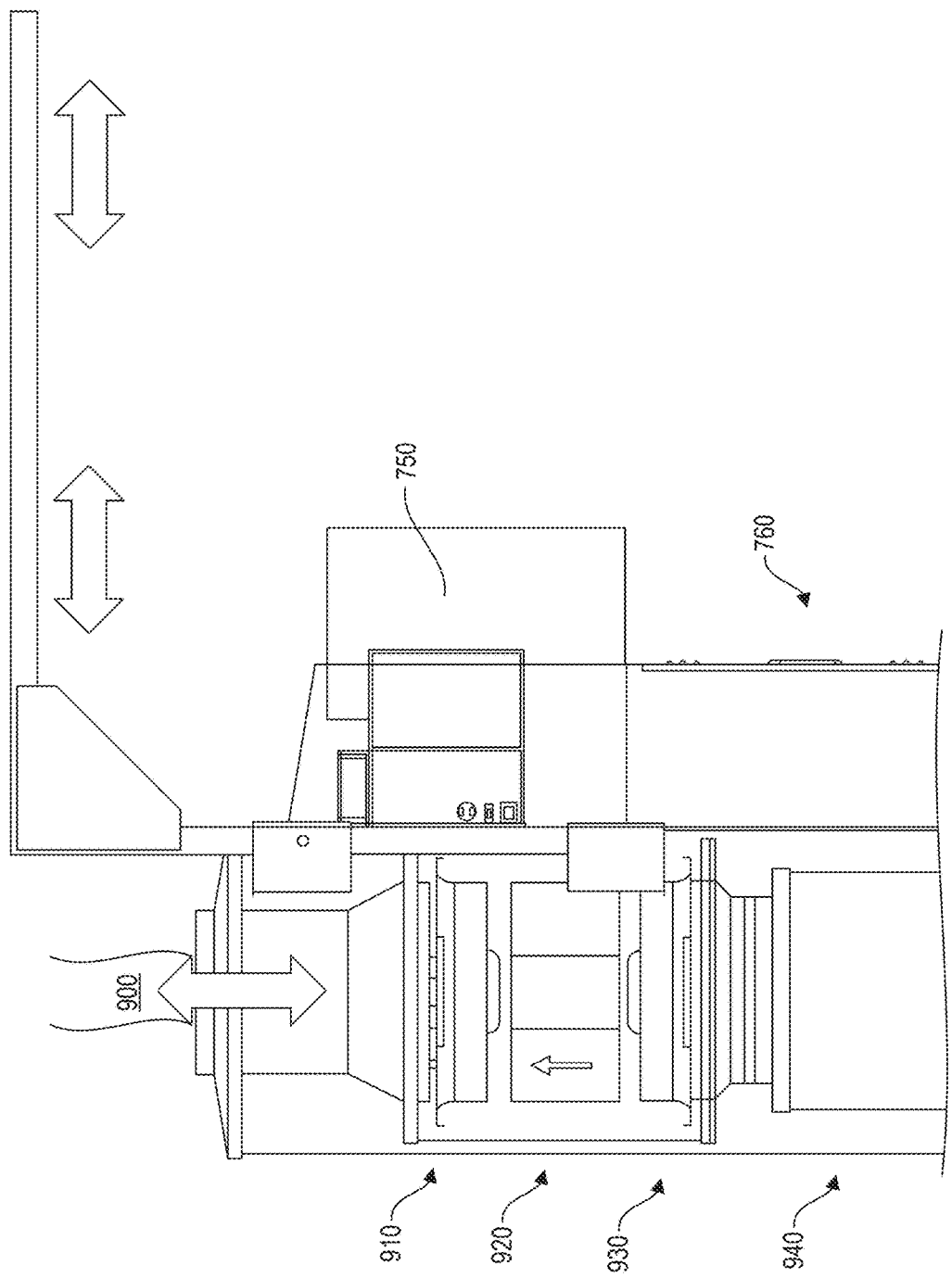
Figure 23A:
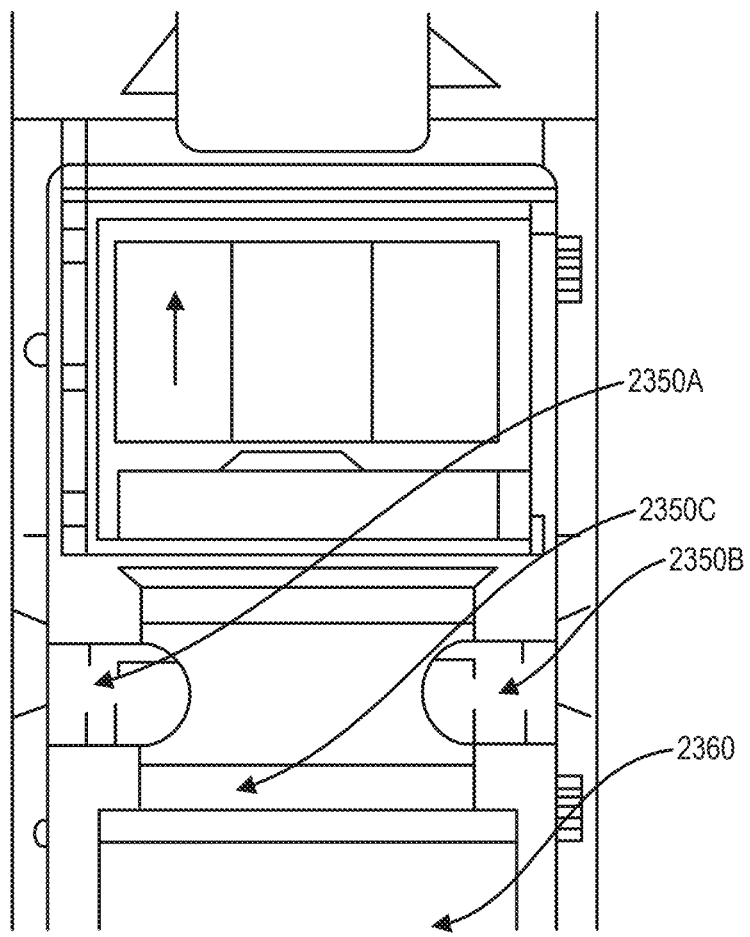
FIG. 23A illustrates another embodiment of a tower system that includes a dual airflow system.

Referring to FIG. 23A, another embodiment of the vertical tower is illustrated which is similar to FIG. 9. As illustrated, the outside air supply for ozone does not pass through the carbon and/or the UV-C filter. The vertical tower may include one or more sets of dampers 2350A, 2350B, 2350C that may selectively open and close a respective passageway for air. The airflow output is preferably filtered by a carbon filter 2360.

Figure 23B:
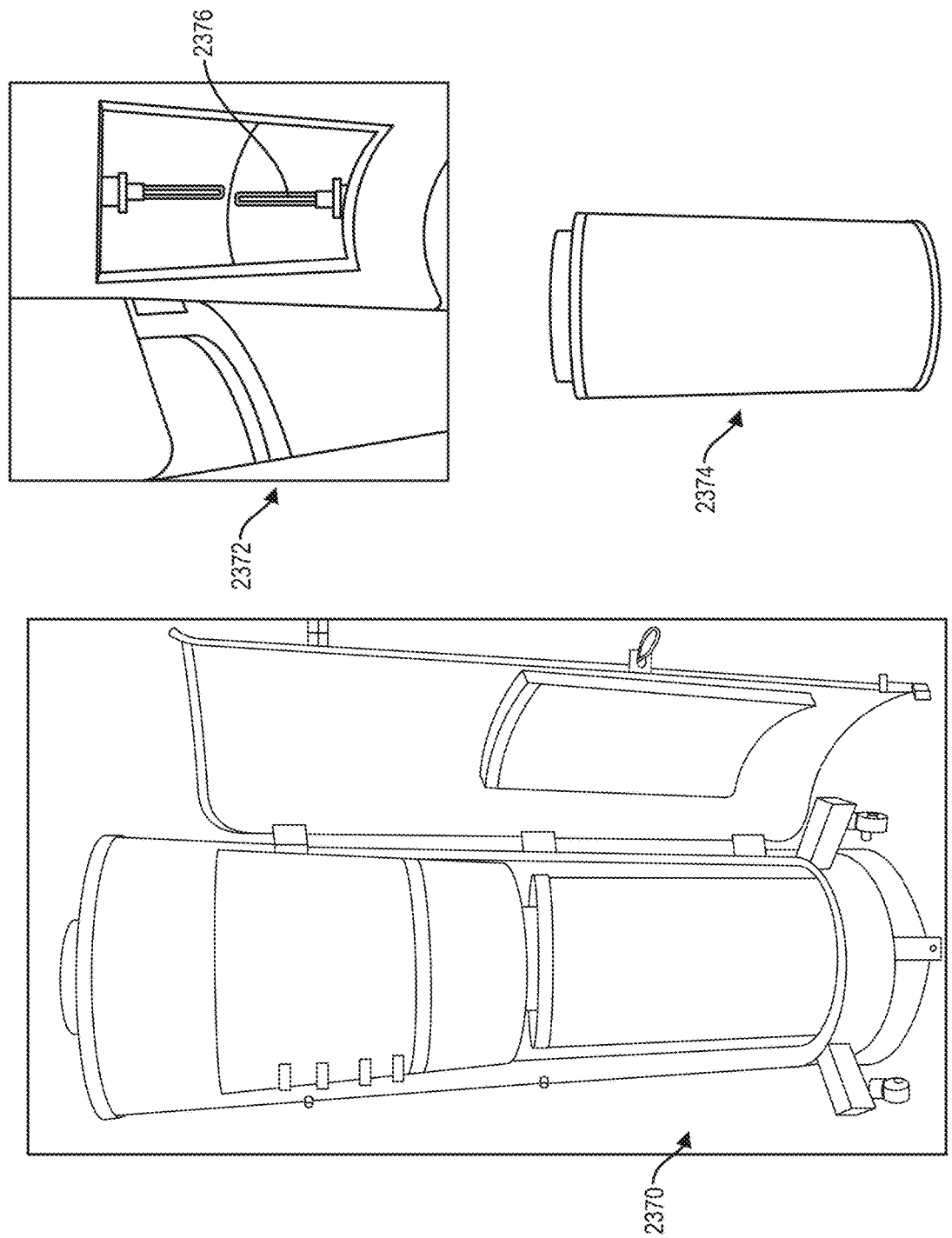
FIG. 23B illustrates another embodiment of a tower system that includes a dual airflow system.

Referring to FIG. 23B, another embodiment of the vertical tower is illustrated which is similar to FIG. 23A. When the air sterilizer fan is pulling air from the top of the vertical tower 2370 then pushing the air through the carbon filter 2374, the air then goes out the HEPA filter 2372 and UV-C sterilizer through the tower door to sterilize the air in the room or to clean the air from ozone inside vehicles. The vertical tower may include a HEPA grade filter 2372 with UV-C sterilizers 2376.

When used for vehicles, one of the airflow paths may provide air with ozone to the vehicle without carbon filtering. When used for vehicles, another of the airflow paths may remove air with ozone from the vehicle together with carbon filtering to neutralize the ozone.

When used for buildings or other structures, one of the airflow paths may provide air with ozone to the environment without carbon filtering. When used for buildings or other structures, another of the airflow paths may remove air with ozone from the environment together with carbon filtering to neutralize the ozone. By way of example, the ozone may be provided to the environment when no people are in the environment, such as between 2-4 AM, and the ozone may be removed thereafter and provide filtering of the air with the carbon filter the remainder of the day.

For example, the tower may include a camera to monitor the environment, if desired. For example, the tower may include a global position system tracking, with an optional external antenna, to permit an accurate location of the tower to be determined at any particular point in time. The tower may further include sensors for carbon monoxide, total volatile organic compounds, ozone, ambient temperature, and humidity. The tower may further include a motion sensor to detect motion. If motion is detected, the ozone generation should be disabled and the UV light source should be enabled to remove the ozone from the environment.

For example, a mobile application may include a dashboard for status view of all registered towers and for adding additional towers, if desired. For example, the mobile application may display sensor status and measurements obtained for each sensor for each tower. For example, the measurements may include ozone, temperature, humidity, carbon monoxide, total volatile organic compounds. The status of each sensor may be categorized and presented to indicate its severity, such as green, yellow, orange, and red (from lowest severity to highest severity). The historical status of each sensor may likewise be presented, such as in chart form. The mobile application may also provide the status of the various components of each tower, such as door open/closed, ozone on/off, UV-C on/off, last motion detected, etc. Moreover, each of the various components may be controlled by the mobile application. Also, the mobile application may include a scheduler to control the various components.

Figure 24A:
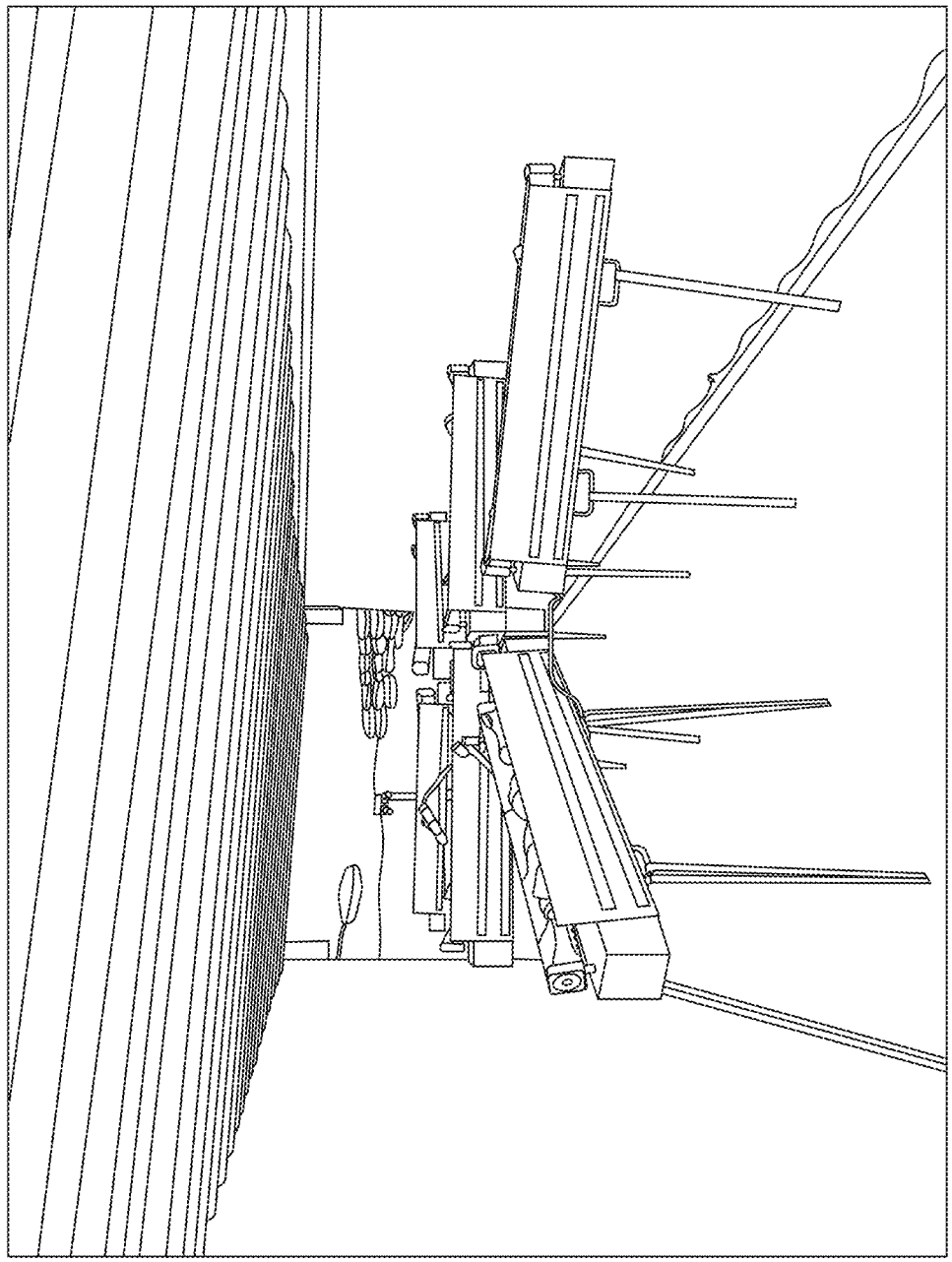
FIG. 24A and FIG. 24B illustrate a conveyor system for sterilization of objects, such as tubes for skis resorts.
Figure 24B:
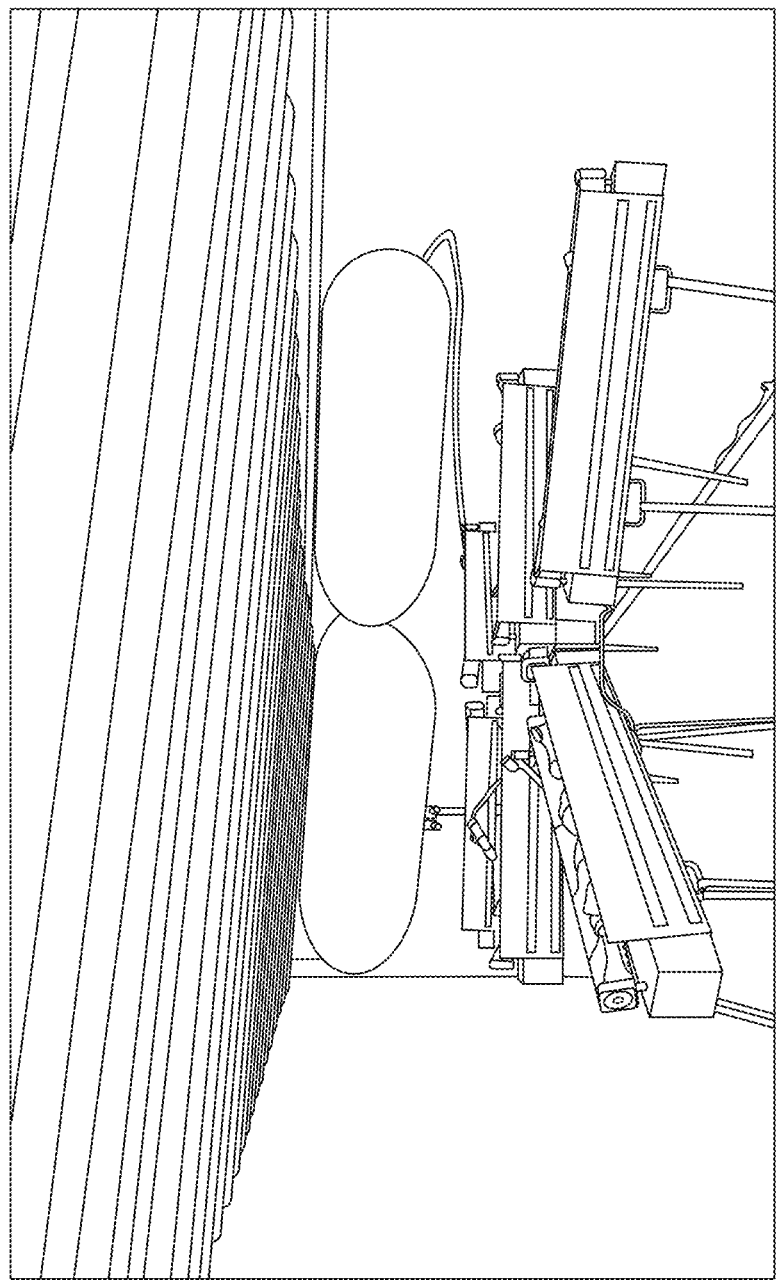

Referring to FIG. 24A and FIG. 24B, a conveyor based system may include one or more conveyors for moving objects thereon. Above the conveyors are a plurality of UV-C light sources that sterilize objects passing thereunder. Preferably, the system is included within a partially enclosed environment, and is sufficiently large to sterilize snow tubes used for tubing on snow. In this manner, the snow tubes may be sterilized before being used by a different person or a different family or different group.

Figure 25:
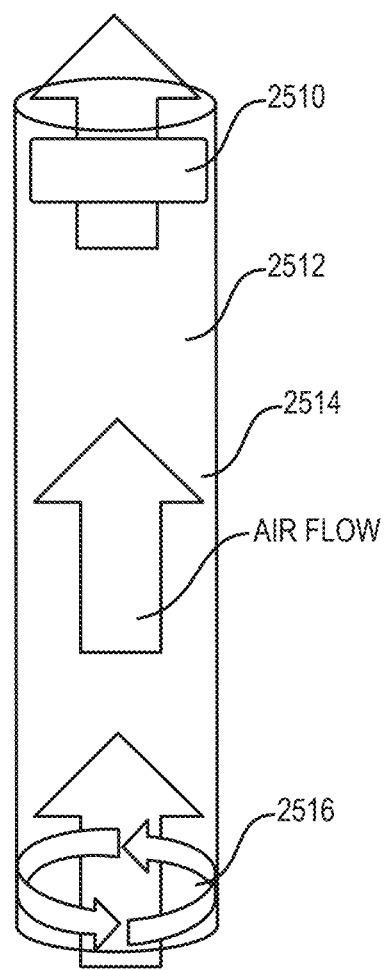
FIG. 25 illustrates another sterilization embodiment.

Referring to FIG. 25, in another embodiment, the interior air sterilizer may be operating when riders are in the vehicle with the doors for the UV-C sterilizer being closed. When there are no riders in the back of the vehicle, the UV-C equipment doors which are directed rearwardly in the vehicle are preferably opened for the UV-C sterilizer light to sterilize the surfaces inside the rear of the vehicle. The sterilizer doors may be opened and closed based upon when motion is detected inside the vehicle rear passenger compartment (e.g., closed when motion is detected and opened when no motion is detected). The sterilizer doors may be opened and closed based upon when the front and/or rear door(s) of the vehicle is opened and/or closed (e.g., closed when the door opening(s) indicates occupancy and opened when the door opening(s) indicates no occupancy). The sterilizer doors may be opened and closed based upon when the front and/or rear door(s) of the vehicle is opened and/or closed (e.g., closed when the door opening(s) indicates occupancy and opened when the door opening(s) indicates no occupancy). The sterilizer doors may be opened and closed based upon a driver based controller (e.g., closed when the vehicle has occupancy in the rear and opened when the vehicle has no occupancy in the rear). The controller may be in the form of a button, a phone application, or otherwise. Also, the vertical sterilizer assists in eliminating odors within the vehicle. The vertical sterilizer may include a HEPA filter 2510, a UV-C equipment sterilizer light with automatic door controls 2512, a motion detector to selectively turn on and/or off the UV-C surface sterilizer 2514, and a fan 2516. By way of example, the UV-C sterilizer may be affixed between the seats of the vehicle, behind the back seat, to the ceiling inside the vehicle, attached to a transparent divider (that moves with the seats) between the seats, or otherwise. By way of example, the transparent divider may be attached to the head rest supports of the front seat.

Figure 26:
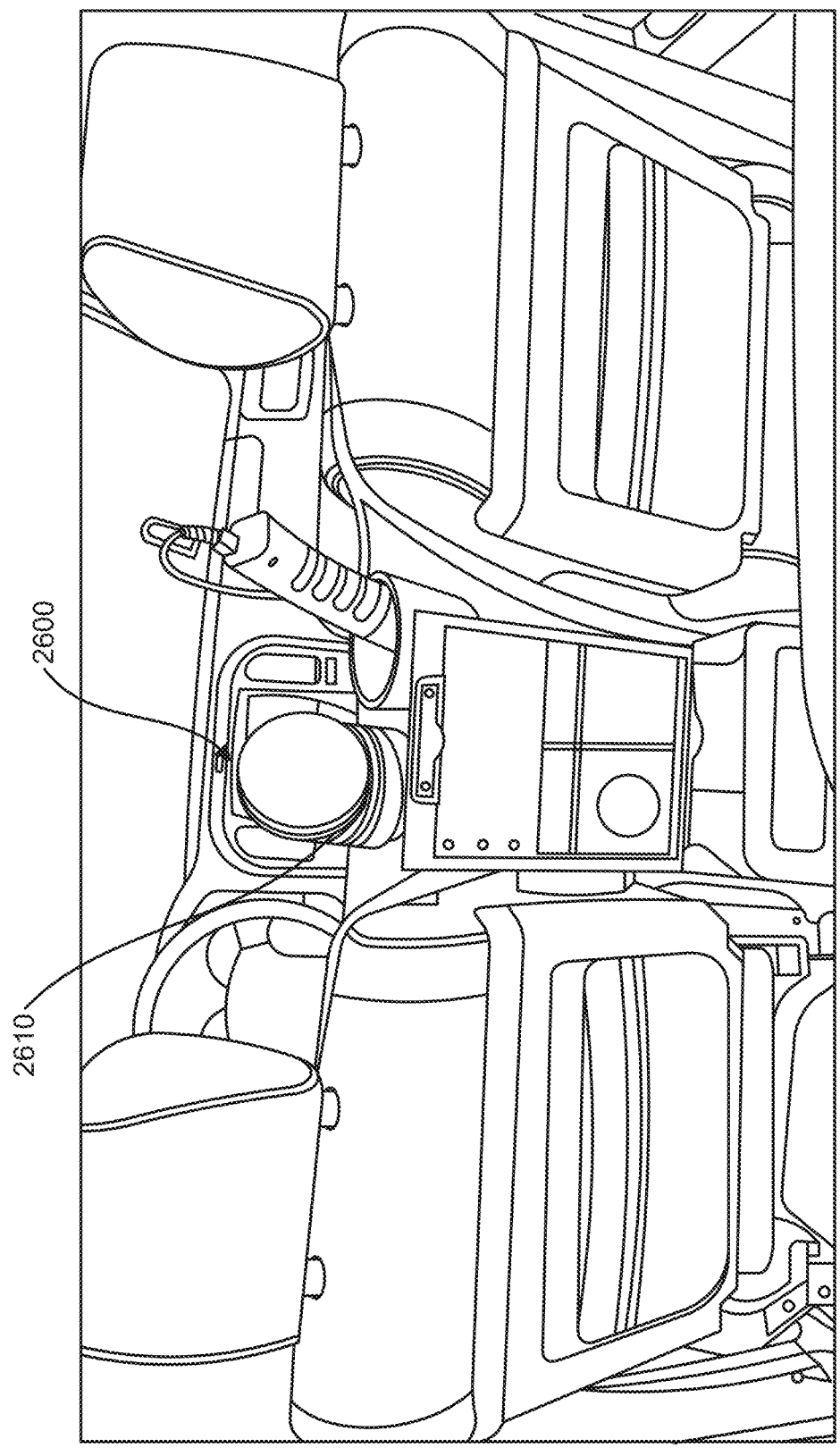
FIG. 26 illustrates a sterilization embodiment with a terminal structure of a flexible hose suitable to engage a face mask.

Referring again to FIG. 26, it was determined that for the air sterilization system the filter has a tendency to become dirty or otherwise the user of the air sterilization system does not have confidence that the filter is sufficiently cleaning the air or otherwise removing viruses, such as covid 19, that could be harmful to the user. To alleviate t\his concern for the user, it is desirable that the air sterilization system includes a terminal structure 2600 on the flexible hose 2610 that is suitable to detachably engage a face mask secured over the end thereof that the user may be wearing or otherwise have in their pocket.

Figure 27:
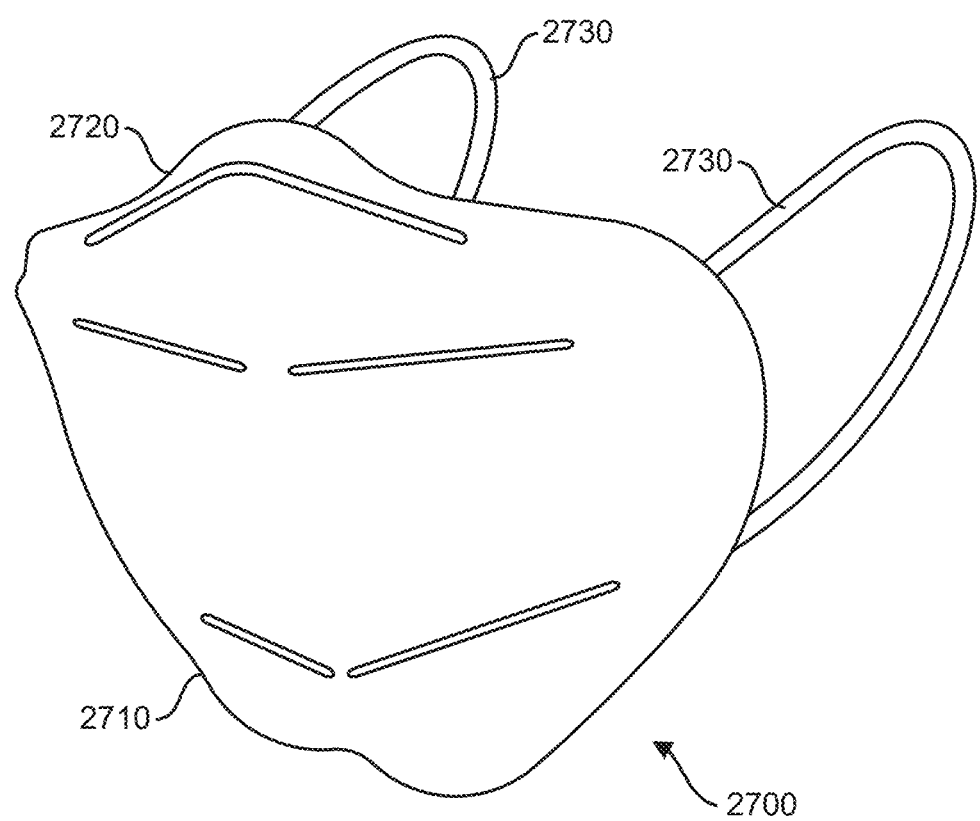
FIG. 27 illustrates a face mask.

Referring to FIG. 27, a face mask 2700 is preferable generally flexible and is foldable about a central vertical axis 2710. The face mask 2700 preferably also includes a flexible material 2720, such as a flexible metal material, that may be bent to a different shape and retains its shape after it is bent. Typically, the flexile material 2720 is bent around the nose of a user to achieve a tighter fit of the mask to the face. The face mask 2700 also preferably includes a pair of elongate loops 2730, that may be stretched and then return to their original shape after being stretched. The principal surface material of the face mask 2700 is preferably an air filtration filter that filters at least 90% and more preferably at least 95% of airborne particles, including dust and liquid droplets in the air, of a size being substantially 0.3 micron in size mass median aerodynamic diameter.

Figure 28:
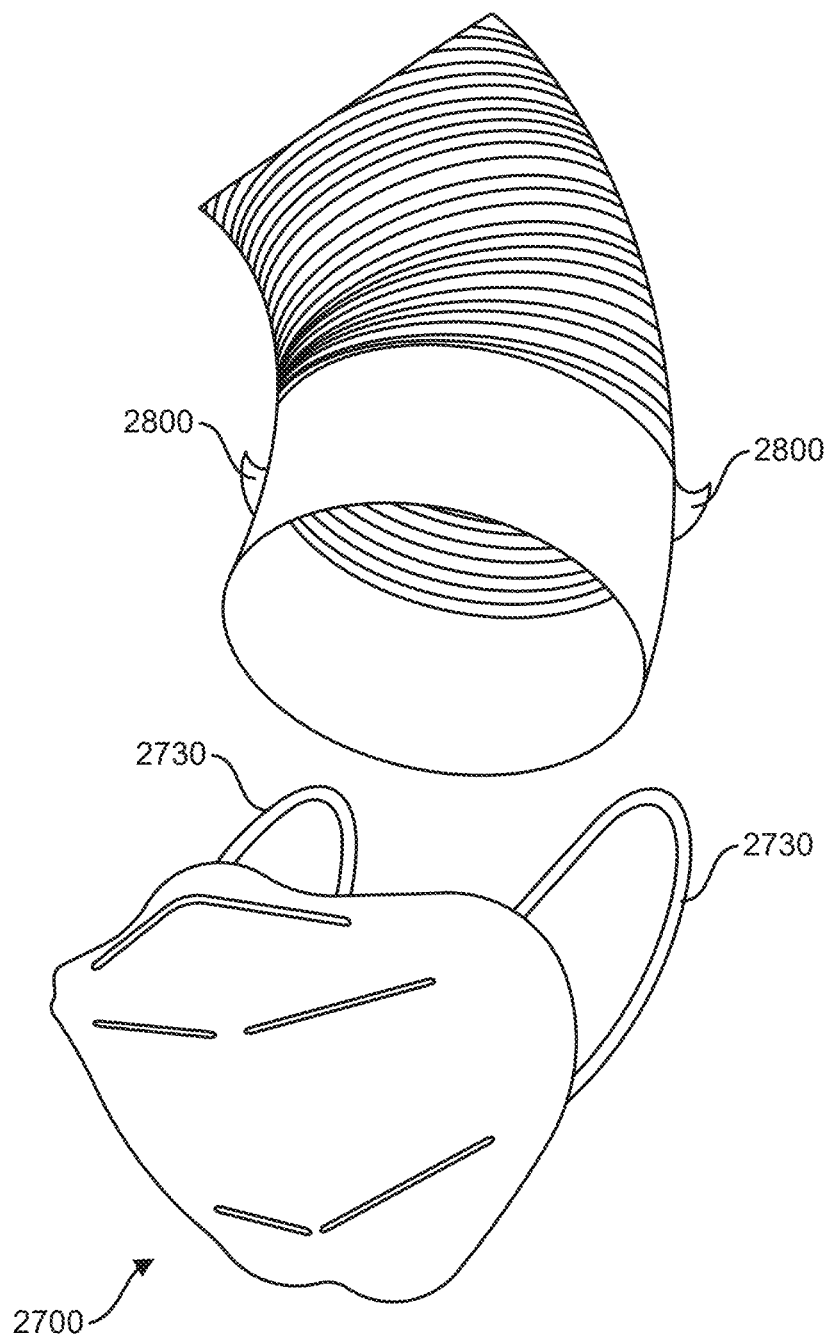
FIG. 28 illustrates the flexible hose suitable to engage the face mask.

Referring to FIG. 28, the end of the flexible hose is preferable circular is cross sectional shape and with a size that will fit completely within the exterior peripheral edge of the face mask 700. In this manner, the face mask will completely fit over the end of the flexible hose. To retain the face mask in position, the flexible hose preferably includes a pair of opposing depressed portions and/or raised portions 2800. The interior of the face mask 2700 is placed over the end of the flexible hose, and the elongate loops 2730 are stretched from their relaxed state, and engaged over and/or within the depressed portions and/or raised portions 2800. In this manner, the face mask is retained by the elongate loops 2730 in a secured fashion to the end of the flexible hose. Also, in this manner, the face mask retained by the elongate loops 2730 may be readily disengaged from the end of the flexible hose. Other retainment structures may likewise be used.

There may be additional components of the invention included with some embodiments. These additional components include, but are not limited to, combinations of a license plate camera or a license plate recognition system, an ultraviolet emitter, a visual indicator, an audible indicator, one or more lockable compartments, a vehicle camera, a security system, and a maintenance system.

The system may be implemented using a computer-readable medium that may be any available medium that may be accessed by the processor. The computer-readable medium may include both a volatile and a nonvolatile medium, a removable and non-removable medium, and a storage medium. The storage medium may include RAM, flash memory, ROM, erasable programmable read-only memory (EPROM), electrically erasable programmable read-only memory (EEPROM), registers, hard disk, a removable disk, a compact disk read-only memory (CD-ROM), or any other form of storage medium. The processor may be operatively coupled via a bus to a display, such as a Liquid Crystal Display (LCD). The display may display information to the user. A keyboard and a cursor control device, such as a touch screen, can also be operatively coupled to bus to enable the user to interface with system, such as using their mobile phone.

The processor may be operatively coupled via the bus to one or more databases. The database may store data in an integrated collection of logically-related records or files. The database may be an operational database, an analytical database, a data warehouse, a distributed database, an end-user database, an external database, a navigational database, an in-memory database, a document-oriented database, a real-time database, a relational database, an object-oriented database, a NoSQL database, or any other database, or any combination thereof.

The memory may store software modules that provide functionality when executed in combination with the processor. The modules can include a data visualization module. The data visualization module may include a data visualization application that can collect, organize, synchronize, and display case data. The data visualization module may comprise a plurality of modules that each provide specific individual functionality for collecting, organizing, synchronizing, entering, modifying, and displaying data. The memory may also store an operating system. The operating system may provide operating system functionality for the system. The memory may also store one or more additional applications to include additional functionality for an overall system.

All the references cited herein are incorporated by reference.

The terms and expressions that have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims that follow.

All the references cited herein are incorporated by reference. The terms and expressions that have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims that follow.

We claim:

1. A sterilizing system for sterilizing a vehicle comprised of:
   (a) a tower, said tower further comprised of:
      (i) a chamber for collecting air, the chamber having an air intake opening and an air output opening interconnected to a tubular hose configured for engagement with an interior of said vehicle;
      (ii) one or more fans configured to pull air into the chamber through the air intake opening and configured to blow air out of the chamber through the air output opening and through the flexible hose in a manner configured for providing said air to the interior of said vehicle;
      (iii) an ozone generator that generates ozone within the chamber that comes into contact with the air collected by the fans, wherein said chamber, said one or more fans, and said ozone generator are enclosed by said tower;
   (b) said tubular hose interconnected to the air output opening and configured to selectively extend between the air output opening and the vehicle;
   (c) said one or more fans configured to blow said air that has been exposed to ozone from said ozone generator as ozonized air out of said chamber through the air output opening and through the flexible hose to the interior of said vehicle;
   (d) said sterilizing system configured to automatically stop blowing said ozonized air through the air output opening and through the flexible hose to the interior of said vehicle after a first predetermined time period has elapsed from initiating said blowing said air that has been exposed to ozone to the interior of said vehicle;
   (e) said sterilizing system configured to automatically stop blowing said ozonized air through the air output opening and through the flexible hose to the interior of said vehicle for a second predetermined time period while previously blown air exposed to ozone in the interior of said vehicle sterilizes the interior of said vehicle after the first predetermined time period has elapsed from stopping said blowing said air that has been exposed to ozone to the interior of said vehicle;
   (f) said one or more fans configured to automatically pull said ozonized air that has been exposed to ozone from said ozone generator from of said interior of said vehicle through the flexible hose into the air output opening for a third predetermined time period after the second predetermined time period has elapsed from said stopping said blowing said air that has been exposed to ozone to the interior of said vehicle, and said pulled ozonized air being discharged from said tower;
   (g) wherein said blowing air into said vehicle for said first predetermined time period, said stopping blowing said air to the interior of said vehicle for said second predetermined time period, and said pulling said ozonized air from said interior of said vehicle, are each automatically initiated without user intervention upon starting said sterilization system to said blowing ozonized air into said vehicle.

2. The sterilizing system of claim 1 further comprising a covering that attaches to the tubular hose and covers some or all of an open window of the vehicle.

3. The sterilizing system of claim 2 further comprising magnets wherein the magnets join the covering to the vehicle.

4. The sterilizing system of claim 1 wherein the one or more fans are further configured to reverse the airflow such that air is pulled into the chamber through the air output opening and blown out of the chamber through the air intake opening.

5. The sterilizing system of claim 4 further comprising one or more carbon filters through which air passes when the airflow is reversed.

6. The sterilization system of claim 1 further comprising an ultraviolet sterilizer positioned at least partially inside the chamber.

7. The sterilization system of claim 6 wherein the ultraviolet sterilizer is removable from its position inside the chamber.

8. The sterilization system of claim 7 wherein the ultraviolet sterilizer further comprises a handle.

* * * * *